(12) United States Patent
Czaja et al.

(10) Patent No.: US 9,090,713 B2
(45) Date of Patent: Jul. 28, 2015

(54) RESORBABLE CELLULOSE BASED BIOMATERIAL AND IMPLANT

(71) Applicant: DePuy Synthes Products, Inc., Raynham, MA (US)

(72) Inventors: Wojciech Czaja, West Chester, PA (US); Dmytro D. Kyryliouk, Philadelphia, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 75 days.

(21) Appl. No.: 13/773,923

(22) Filed: Feb. 22, 2013

(65) Prior Publication Data
US 2013/0224278 A1      Aug. 29, 2013

Related U.S. Application Data

(60) Provisional application No. 61/601,653, filed on Feb. 22, 2012.

(51) Int. Cl.
| | |
|---|---|
| *A61F 2/00* | (2006.01) |
| *C08B 15/02* | (2006.01) |
| *A61L 27/20* | (2006.01) |
| *A61L 27/58* | (2006.01) |
| *A61L 31/04* | (2006.01) |
| *A61L 31/14* | (2006.01) |

(52) U.S. Cl.
CPC ............... *C08B 15/02* (2013.01); *A61L 27/20* (2013.01); *A61L 27/58* (2013.01); *A61L 31/042* (2013.01); *A61L 31/148* (2013.01)

(58) Field of Classification Search
CPC ......... C08B 15/02; A61L 27/20; A61L 27/58; A61L 31/042; A61L 31/148; C08L 1/04; A61F 2/00
USPC ........................................................ 424/426
See application file for complete search history.

(56) References Cited

U.S. PATENT DOCUMENTS

| | | | |
|---|---|---|---|
| 6,800,753 B2 | 10/2004 | Kumar | |
| 7,374,775 B2 | 5/2008 | Damien et al. | |
| 7,510,725 B2 | 3/2009 | Damien et al. | |
| 7,709,631 B2 | 5/2010 | Harris et al. | |
| 8,110,222 B2 * | 2/2012 | Hutchens et al. | 424/489 |
| 8,198,261 B2 * | 6/2012 | Damien et al. | 514/57 |
| 2007/0213522 A1 * | 9/2007 | Harris et al. | 536/56 |
| 2007/0286884 A1 * | 12/2007 | Serafica et al. | 424/423 |

FOREIGN PATENT DOCUMENTS

| | | |
|---|---|---|
| EP | 2 198 895 | 6/2010 |
| WO | WO 2005/018492 | 3/2005 |
| WO | 2010/052585 * | 5/2010 |
| WO | WO 2010/052582 | 5/2010 |
| WO | WO 2010/052583 | 5/2010 |
| WO | WO 2010/052585 | 5/2010 |

OTHER PUBLICATIONS

Alvarez et al, Effectiveness of a Biocellulose Wound Dressing for the Treatment of Chronic Venous Leg Ulcers: Results of a Single Center Random, Wounds, Jul. 2004,16, 224-233.
Bodin et al, Bacterial cellulose as a potential meniscus implant, J Tissue Eng. and Regen. Med., Sep./Oct. 2007, 1(5), 406-408.
Calvini et al., FTIR and WAXS analysis of periodate oxycellulose: Evidence for a cluster mechanism of oxidation, Vibrational Spectroscopy, Mar. 2006, 40, 177-183.
Czaja, et al., The future prospects of microbial cellulose in biomedical applications, Biomacromolecules, Jan. 2007, 8(1),1-12.
Devi, Biosoluable surgical material from 2, 3-diadehyde cellulose, Biomaterials, May 1986 193-196.
Driscoll, Electron beam irradiation of cellulose, Radiation Physics and Chem., Jul./Aug. 2009, 539-542.
Fontana et al, Acetobacter cellulose pellicle as a temporary skin substitute, Appl. Biochem. Biotechnol. Spring/Summer 1990, 24/25, 253-264.
Hu et al, In vitro biodegradability and mechanical properties of bioabsorbable bacterial cellulose incorporating cellulases, Acta Biomater, Jul. 2011, 7(7), 2835-45.
Kim et al, Periodate oxidation of crystalline cellulose, Biomacromolecules, Fall 2000 1(3), 488-92.
Klemm et al, Cellulose: fascinating biopolymer and sustainable raw material, Angew Chem Int Ed Engl, May 30, 2005, 44(22), 3358-93.
Laurence et al, Development of a resorbable macroporous cellulosic material used as hemostatic in an osseous environment, J Biomed. Mater. Res. A., Jun. 15, 2005, 73(4), 422-9.
Losquadro et al, Polylactide-co-glycolide Fiber-Reinforced Calcium Phosphate Bone Cement, Arch Facial Plast Surg, 11(2), Mar/Apr. 2009, 104-109.
Mester, The Formazan reaction in providing the structure of periodate oxidized polysaccharides, J. Chemical Society, Oct. 1955, 5452-5453.
Nevell T., Oxidation, Methods in Carbohydrate Chemistry, New York: Academic Press, 1963, 3, 164-185.

(Continued)

*Primary Examiner* — Suzanne Ziska
(74) *Attorney, Agent, or Firm* — Baker & Hostetler LLP

(57) ABSTRACT

The present disclosure describes an implant for tissue replacement or augmentation including a resorbable non-pyrogenic porous body of irradiated oxidized cellulose, formed from a precurosr reactive mixture of irradiated cellulose and an oxidizing agent, where the body forms a heterogeneous three-dimensional fibrillar network. Also disclosed is a method for producing a body of oxidized cellulose including irradiating a body of cellulose to form an irradiated body of cellulose, and reacting the irradiated body of cellulose with an oxidizing agent to form a non-pyrogenic porous and resorbable body of oxidized cellulose.

42 Claims, 17 Drawing Sheets

(56) References Cited

OTHER PUBLICATIONS

Nishi, The structure and mechanical properties of sheets prepared from bacterial cellulose, J. Materials Science, Jun. 1990, 2997-3001.

O'Sullivan, Cellulose: the structure slowly unravels, Cellulose, Jun. 1997, (4), 173-207.

Roychowdhury et al, Fabrication and evaluation of porous 2,3-dialdehydecellulose membrane as a potential biodegradable tissue-engineering scaffold, J Biomed Mater Res A., Feb. 2006, 76(2), 300-9.

Shah et al, Towards electronic paper displays made from microbial cellulose, Appl Microbiol Biotechnol, Jan. 2005, 66(4), 352-5.

Singh et al, Biodegradation studies on periodate oxidized cellulose, Biomaterials, Jan. 1982, 3(1), 16-20.

Stilwell et al, Oxidized cellulose: Chemistry, Processing and Medical Applications, Handbook of Biodegradable Polymers, 1997, 291-306.

Svensson et al, Bacterial cellulose as a potential scaffold for tissue engineering of cartilage, Biomaterials, Feb. 2005, 26(4), 419-31.

Timmer et al, In vitro cytotoxicity of injectable and biodegradable poly(propylene fumarate)-based networks: unreacted macromers, cross-linked networks, and degradation products, Biomacromolecules, Jul./Aug. 2003, 4(4),1026-33.

Vicini, Thermal analysis and characterization of cellulose oxidized with sodium methaperiodate, Thermochimica Acta, Mar. 5, 2004, 123-130.

* cited by examiner

RESORBABLE CELLULOSE BASED BIOMATERIAL AND IMPLANT

CROSS-REFERENCE TO RELATED APPLICATION

This application claims priority to U.S. Provisional Application Ser. No. 61/601,653, filed Feb. 22, 2012, the disclosure of which is hereby incorporated by reference as if set forth in its entirety herein.

FIELD OF THE DISCLOSURE

The present disclosure relates to a resorbable, porous and conformable biomaterial for use as a medical implant and a controlled oxidation process of γ-irradiated cellulose to provide the same. The implant can be formed as a sheet or patch for use in tissue replacement or augmentation, particularly for soft tissue indications and more particularly for use with dura mater.

BACKGROUND

Repair of the dura (duraplasty) is indicated following traumatic, neoplastic, or inflammatory destruction, surgical excision, or congenital absence. Dural replacements are used in cranial surgery when primary closure of native dura is not possible. Historically, numerous materials have been used including metal foils, human tissues, animal tissues (porcine dermis, bovine collagen and pericardium) and polymers (PTFE, polyglactin, hydroxyethylmethacrylate). Animal tissues remain the best of the currently available materials with bovine pericardium and bovine collagen being the market leaders (e.g., Duragen®, Duraform®). However, the animal material carries the possibility of infection by prions that may cause mad cow disease. Also, bovine collagen often resorbs within two weeks, prior to complete healing of the dura. Additionally, bovine pericardium is sometimes cross-linked with glutaraldehyde, which has natural biotoxicity. Synthetic materials have handling deficiencies and may cause cerebrospinal fluid (CSF) leakage if not properly sutured in place.

Cellulose of various origins has been proven to be a versatile biomaterial. Synthesized by just about every type of plant and a select number of bacteria, it is a natural, renewable, biocompatible, and biodegradable polymer used in a wide variety of applications.

However, native cellulose cannot be resorbed in human body due to the lack of enzymatic machinery able to break down its highly crystalline structure, which is stabilized by inter and intra hydrogen bonds. Resorbability of cellulose can, however, be achieved through oxidation using various chemicals, including metaperiodate, hypochlorite, dichromate, or nitrogen dioxide (see Stilwell et al., *Oxidized cellulose: Chemistry, Processing and Medical Applications, Handbook of Biodegradable Polymers:* 1997, 291-306.). Oxidized plant cellulose has been successfully used as a resorbable hemostat (Johnson and Johnson's Surgicel® since 1949 and more recently by Gelita Medical's Gelitacel® since 2006). Products consisting of plant based oxidized cellulose are commonly used as hemostatic agents, wound dressings and anti-adhesion barriers (see U.S. Pat. No. 6,800,753; Stilwell et al., 1997).

Plant cellulose is oxidized most effectively through the use of nitrogen dioxide gas vapor. However, there are toxic effects to be considered from the use of nitrogen dioxide gas; whereas sodium metaperiodate has proven to be more selective when oxidizing highly crystalline celluloses with minimal side reactivity (see Nevell T., *Oxidation, Methods in Carbohydrate Chemistry*, New York: Academic Press 1963; 3: 164-185). Its oxidizing effects and methods of use have been studied extensively on plant cellulose (see Stilwell et al., 1997; Kim et al., *Periodate oxidation of crystalline cellulose*, Biomacromolecules 2000; 1: 488-492; Calvini et al., *FTIR and WAXS analysis of periodate oxycellulose: Evidence for a cluster mechanism of oxidation*, Vibrational Spectroscopy 2006; 40: 177-183.; Singh et al., *Biodegradation studies on periodate oxidized cellulose*, Biomaterials 1982; 16-20; Devi et al., *Biosoluble surgical material from 2,3-dialdehyde cellulose*, Biomaterials 1986; 7: 193-196.; Laurence et al., *Development of resorbable macroporous cellulosic material used as hemostatic in an osseous environment*, J Biomed Mater Res 2005; 73A: 422-429; Roychowdhury and Kumar, *Fabrication and evaluation of porous 2,3-dialdehyde cellulose membrane as a potential biodegradable tissue-engineering scaffold*, J Biomed Mater Res 2006; 76A: 300-309.). The mechanism of oxidation using periodate relies on cleavage of the C2-C3 bond in the glucopyranose ring and formation of dialdehyde groups. Such a dialdehyde cellulose is believed to degrade by hydrolysis under physiological conditions seen in the body into 2,4-dihydroxybutyric acid and glycolic acid (see Singh et al, 1982). Both of these degradation products are known to be biocompatible and biodegradable and can be metabolized by the body (see Devi et al., 1986; Singh et al., 1982). Once the degradation process is initiated it continues along the glucan chains that comprise the cellulose network (see Stilwell et al., 1997).

Methods for oxidation of bacterially-derived cellulose have also been described in U.S. Pat. No. 7,709,631. Bacterially-derived cellulose possesses unique physical and mechanical properties which results from its three-dimensional structure. Due to its handling characteristics, biocompatibility, and safety, it is already used in several medical devices, for example as described in U.S. Pat. Nos. 7,374,775 and 7,510,725. One type of microbial cellulose synthesized by *Acetobacter xylinum* (reclassified as *Gluconacetobacter xylinus*) is characterized by a highly crystalline three-dimensional network consisting of pure cellulose nanofibers. Microbial cellulose has long been recognized as a biomaterial with potential applications for temporary wound coverage, for treatment of chronic wounds and burns, and as a scaffold for tissue growth, synthetic blood vessels, as well as many other biomedical applications (Fontana et al., *Acetobacter cellulose pellicle as a temporary skin substitute*, Appl Biochem Biotechnol 1990; 24/25: 253-264; Alvarez et al, *Effectiveness of a Biocellulose Wound Dressing for the Treatment of Chronic Venous Leg Ulcers: Results of a Single Center Random*, Wounds 2004; 16: 224-233; Czaja et al., *The future prospects of microbial cellulose in biomedical applications*, Biomacromolecules 2007; 8(1): 1-12; Klemm et al., *Cellulose: Fascinating Biopolymer and Sustainable Raw Material*, Angew Chem, Int Ed 2005; 44: 3358-3393; Bodin et al., *Bacterial cellulose as a potential meniscus implant*, J Tissue Eng and Regen Med 2007; 1(5): 406-408; Svensson et al., *Bacterial cellulose as a potential scaffold for tissue engineering of cartilage*, Biomaterials 2005; 26 (4): 419-431).

Although methods for oxidizing cellulose are widely described in the literature they often do not result in homogenously oxidized materials with the most desirable properties for medical applications. It is particularly true for soft tissue applications, for example dural repair applications, where the material needs to be able to rehydrate, readily conform to the various contours of the body, have adequate strength to allow easy handling, but also to be resorbable over a time frame that is compatible with healing of the particular anatomical site.

Consequently there is a need for oxidized cellulose biomaterials and methods for producing the same that can achieve these desired properties.

The ideal material should be able to prevent CSF leakage, have good biocompatibility, be free of potential risk of infection, have good intra-operative handling, have mechanical properties similar to dura, have a resorption profile beneficial to tissue regrowth, and be readily available and storable.

SUMMARY

The present disclosure describes an irradiated oxidized cellulose for use as a resorbable biomaterial that is formed from a precursor rective mixture of an irradiated cellulose and an oxidizing agent. The reaction product thereof is a resorbable biomaterial that is non-pyrogenic and can be porous. According to one embodiment, the irradiated cellulose is microbial-derived cellulose, and in a preferred embodiment is derived from *Gluconacetobacter xylinus*. The resorbable biomaterial as described can have a variable range of degree of oxidation, which can, according to one embodiment, be in the range of about 0 percent to about 99 percent oxidation, for example in the range of about 20 percent to about 70 percent.

The present disclosure additionally describes a medical implant for use in tissue repair, replacement or augmentation formed from a porous body of irradiated-oxidized cellulose, that, according to one embodiment, can be formed by reacting irradiated cellulose with an oxidizing agent. The oxidized cellulose body that forms the implant has a chaotic, heterogeneous three-dimensional fibrillar network that can allow the implant to rapidly transition from a first rigid (dehydrated) state to a second hydrated state upon contact with biocompatible fluids (e.g., water, saline, blood, cerebrospinal fluid etc.). The implant in the hydrated state can, according to one embodiment, have a surface that is conformable to an anatomical surface, preferably a soft tissue surface, and more preferably to a dural tissue surface. According to another embodiment, the surface of the implant can be conformable to a secondary medical device. According to a further embodiment, the implant can be a scaffold or carrier for an active agent. For example, the active agent can be impregnated within the porous body of the implant, or coated onto a surface of the implant, or both. According to one embodiment, the active agent can be impregnated within and/or coated onto the implant substantially at or near the time of implantation (i.e., intraoperatively). In an alternative embodiment, the active agent can be impregnated within and/or coated onto the implant prior to the time of implantation (i.e., preoperatively). In certain embodiments, more than one active agent can be impregnated within and/or coated onto the implant, and further the more than one active agents can be impregnated within and/or coated onto the implant at different time periods. For example, some active agents can be preoperatively combined with the implant, while other active agents can be combined intraoperatively.

The present disclosure further describes a method of producing a body of oxidized cellulose that is porous and resorbable including:

(a) irradiating a body of cellulose so as to form an irradiated body of cellulose, and (b) reacting the irradiated body of cellulose with an oxidizing agent so as to form a body of oxidized cellulose.

The body of oxidized cellulose formed can be, according to one embodiment, porous, non-pyrogenic, and resorbable.

According to one embodiment, the method can further include the step of partially dehydrating the body of irradiated cellulose, preferably by mechanically pressing the cellulose body. According to another embodiment, the method can further include the step of at least partially dehydrating the body of oxidized cellulose, preferably by critical point drying using supercritical carbon dioxide. According to an additional embodiment, the step of irradiating the non-pyrogenic body can include one, or alternatively more than one, doses or exposures of radiations.

BRIEF DESCRIPTION OF THE DRAWINGS

The drawings illustrate generally, by way of example, but not by way of limitation, various embodiments discussed in the present document. The foregoing summary, as well as the following detailed description of preferred embodiments of the application, will be better understood when read in conjunction with the appended drawings.

DETAILED DESCRIPTION

Figure 1:
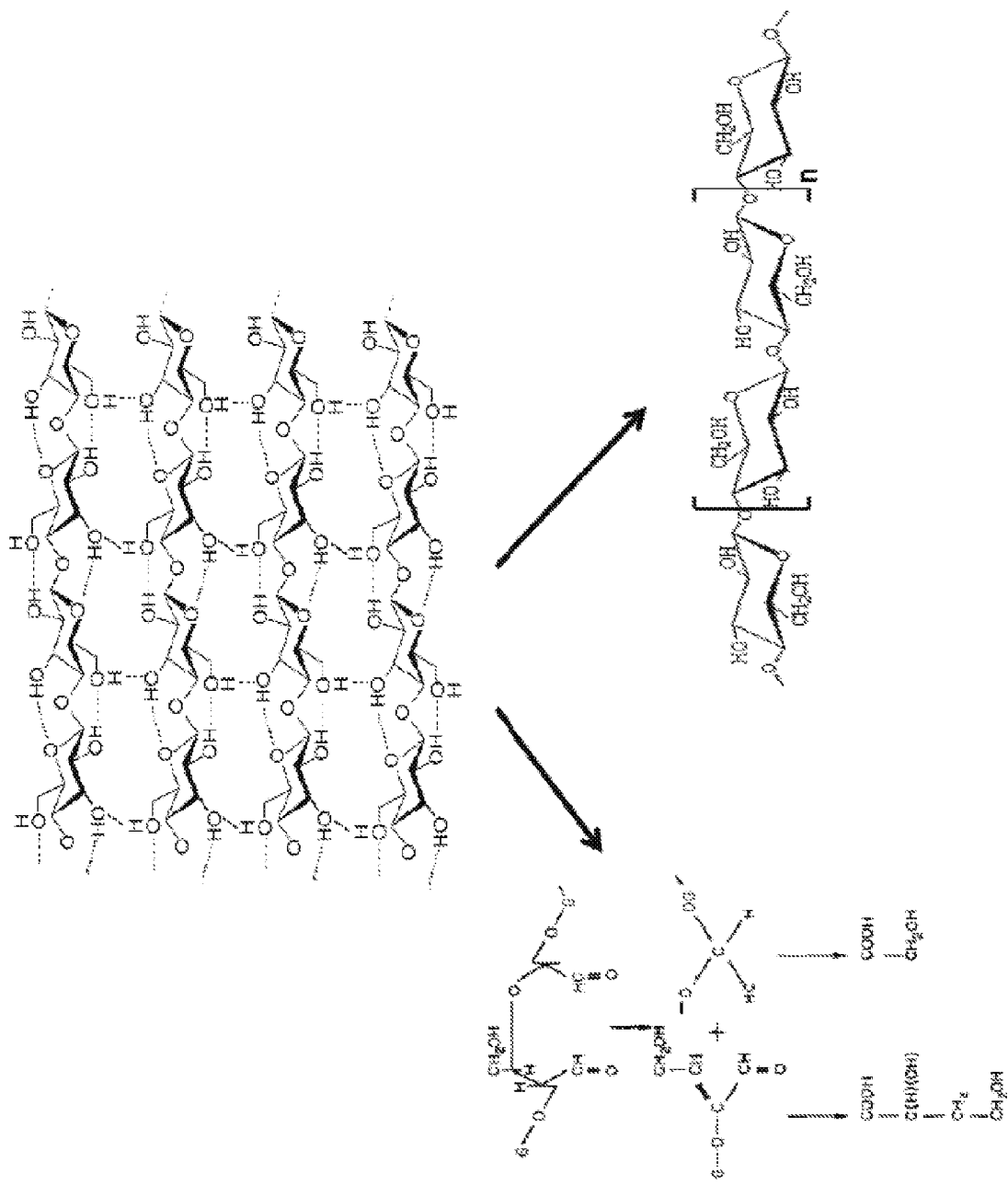
FIG. 1 is a graphical depiction of proposed in vivo degradation of oxidized cellulose.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable. Further, reference to values stated in ranges includes each and every value within that range. It is also to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination As used herein, "body of cellulose" and derivations and variations thereof, for example "cellulose body," "body of irradiated cellulose," "body of oxidized cellulose," "body of microbial cellulose," etc. is meant to describe a mass of cellulose in any type of shape or spatial arrangement, and is not intended to limit the mass of cellulose to any particular orientations or configurations, unless otherwise explicitly stated herein. Non-limiting examples of bodies of cellulose according to the present disclosure can include a sheet of cellulose, a cellulose membrane, a pellicle of cellulose, a cellulose film, a cellulose patch and/or a cellulose sample.

As used herein "native cellulose", and derivations and variations thereof, is meant to describe cellulose, both plant and microbial originated forms, that are in an unadulterated state. For example, in certain embodiments described herein "native cellulose" refers to celluloses of any origin that have not been subjected to any forms of oxidation or irradiation.

According to the present disclosure, a resorbable biomaterial of irradiated oxidized cellulose is described that is formed from a precursor rective mixture of an irradiated cellulose and an oxidizing agent. The reaction product thereof is a resorbable biomaterial that is non-pyrogenic and can be porous. Cellulose can be derived from either plant or microbial sources. According to one embodiment, the irradiated cellulose is a microbial-derived cellulose, and preferably is derived from *Gluconacetobacter xylinus.*

Any suitable oxidizing agent can be used in the reactive mixture to react with the irradiated cellulose according to the present disclosure. Some examples of suitable oxidizing agents can include metaperiodate, hypochlorite, dichromate, peroxide, permanganate or nitrogen dioxide. A preferred oxidizing agent is sodium metaperiodate. The oxidizing agent can have, according to one embodiment, a concentration range of about 0.01M to about 10.0M, preferably about 0.05M to about 1.0M, and more preferably from about 0.1M to about 0.5M.

Irradiation of a cellulose body can effect changes in a subsequent oxidation reaction by providing chemical, structural and morphological changes within the cellulose body's fiber network. For example, radiation treatment can, among other things, increase cationic permselectivity, membrane conductivity, and cause interhydrogen bonding changes. Radiating cellulose's chemical structure of glucopyranose chains can decrease cellulose crystallinity and average molecular weight, and increases the available surface area. Without being bound by any particular theory, it is believed that the chemical and physical changes of the cellulose membrane that may result from treatment with irradiation make it more amenable to chemical treatment; i.e., oxidation. It is also further believed that irradiation of the cellulose membrane prior to oxidation results in a porous biomaterial having shorter and more efficiently oxidized glucopyranose chains which are more easily accessible by biocompatible fluids. In contrast, it is expected that a non-irradiated oxidized cellulose has, on average, longer glucopyranose chains that contain more randomly scattered dialdehyde groups and also continues to maintain a relatively high crystalline structure. Shorter glucose chains formed from irradiation can therefore result in a body of cellulose having a greater overall amount of oxidized cellulose than can be achieved in oxidation of a corresponding non-irradiated cellulose body. A higher percentage of oxidized glucose chains can lead to a more rapid and homogenous degradation of the irradiated oxidized cellulose body. As previously noted, and depicted in FIG. 1, it is hypothesized that in vivo degradation of oxidized cellulose occurs primarily by hydrolysis into 2,4-dihydroxybutyric acid and glycolic acid. Up to 90% of the degradation of the cellulose body can occur in this manner. Once the degradation process is initiated it continues along the glucose chains that comprise the cellulose body. Additional degradation, which can account for the remaining 10% of the cellulose body, also occurs where hydrolysis of the dialdehyde groups has fractured the large glucose chains into smaller poly or oligosaccharide units which are further cleared from the body through phagocytosis.

The non-pyrogenic resorbable biomaterial as described can have a variable range of degree of oxidation, which can, according to one embodiment, be in the range of about 0 percent to about 99 percent oxidation, for example in a range of about 20 percent to about 70 percent. The degree of oxidation of the irradiated oxidized cellulose can depend on the oxidizing agent selected, the concentration range of the oxidizing agent, reaction temperature, and the time period of the reaction between the irradiated cellulose and the oxidizing agent. According to one embodiment, the degree of oxidation is in the range of about 15 percent to about 80 percent, and in another embodiment is in the range of about 20 to about 70 percent.

Figure 2:
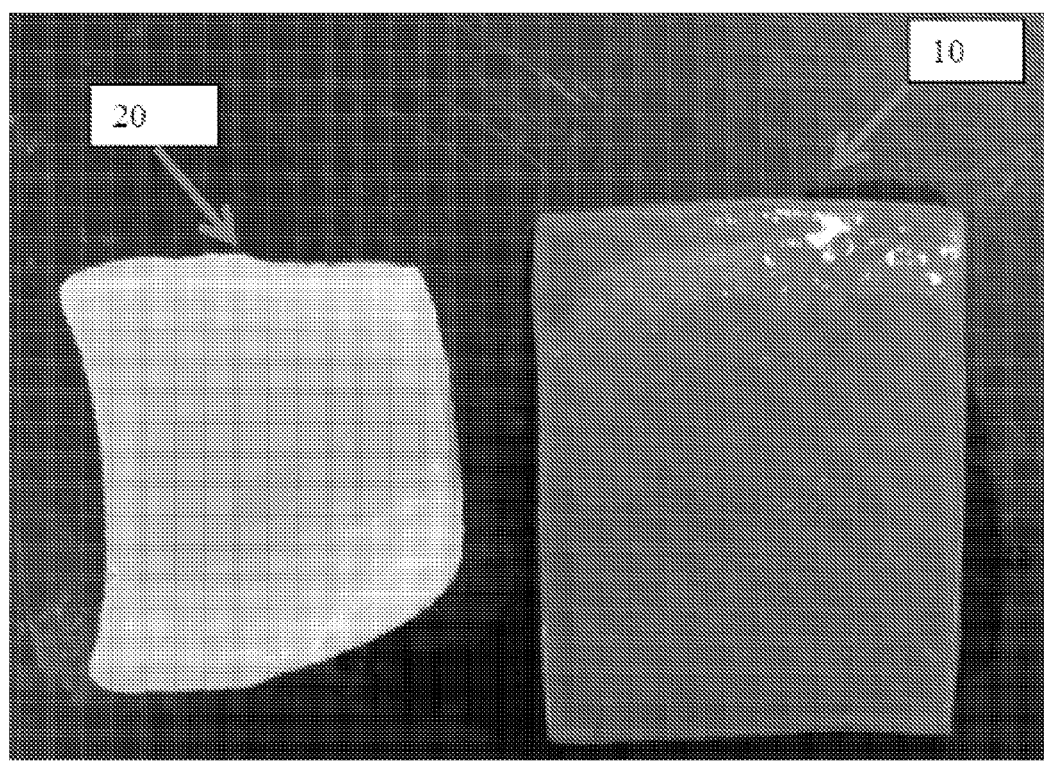
FIG. 2 is a top view, side-by-side photo of an irradiated oxidized cellulose implant according to the disclosure in a hydrated state and a comparative non-irradiated oxidized cellulose implant also in a hydrated state.

According to the present disclosure, an implant is described having sufficient mechanical strength, conformability to anatomical surfaces, and resorption profile for use in tissue repair, replacement and/or augmentation procedures, particularly soft tissue applications, and more particularly for use as a dural replacement patch. The implant includes a porous body of irradiated oxidized cellulose formed by reacting irradiated cellulose with an oxidizing agent. The porous body of cellulose is non-pyrogenic and has a heterogeneous three-dimensional fibrillar network of cellulose that can transition from a first rigid (dehydrated) state to a second hydrated state upon contact with biocompatible fluids (e.g., water, saline, blood, CSF etc.). FIG. 2 is a top view of an implant 10 according to one embodiment of the present disclosure in a hydrated state and a non-irradiated oxidized cellulose implant 20 in a hydrated state. The implant 10 in the second hydrated state can, according to one embodiment, be translucent, as shown in FIG. 2, and be in the form of a cellulose patch. As used herein "translucent" refers to the ability of the implant, in a hydrated state, to allow light to pass through in a diffused manner so that a field is illuminated but objects cannot necessarily be seen distinctly through the implant.

The porous characteristic of the implant both permits rapid uptake of fluid (hydration) as well as allowing tissue ingrowth when implanted. According to one embodiment, the implant in the hydrated state has sufficient durability and burst strength (explained in further detail below) to be manipulated and implanted to a desired anatomical location and exhibits desired adherence and attachment to both regular and irregular contoured anatomical surfaces. According to one embodiment, a surface of the implant in the hydrated state is conformable (explained in further detail below) to an anatomical surface, preferably a surface of a soft tissue and more preferably a dural tissue surface. The implant can, in a further embodiment, adhere to an anatomical surface without the aid of suturing or securing devices; i.e., the implant can be self-adhering/self-securing. It should be appreciated, however, that the implant can be secured to an anatomical surface with the aid of suturing or securing devices if so desired.

In certain medical procedures, it is desirable to have additional medical devices present at the anatomical location in order to provide additional support, fixation and/or stabilization at the locus of repair. Where such secondary medical devices are desired, the implant surface in the hydrated state can be conformable to the anatomical surface, the secondary medical device surface, and/or both surfaces. Example of suitable secondary medical devices can include, but are not limited to, bone screws, bone plates, metallic and polymer meshes, as well as metallic and polymer plates and caps such as those used in cranial surgeries.

The porous body of irradiated oxidized cellulose that forms the implant has the ability, according to one embodiment, to transition from a first rigid (dehydrated) state to a second hydrated state upon contact with a biocompatible fluid. An implant in the second hydrated state has conformability to an anatomical surface as is described below in further detail. In certain embodiments, the transition can occur in a short time period. For example, according to one embodiment, the implant can transition from a first rigid state to a second hydrated state within about less than 10 minutes. According to further embodiments, the implant can transition from a first rigid state to a second hydrated state (e.g., fully hydrated) within about less than five minutes, within about less than 30 seconds, within about less than 10 seconds, within about less than 5 seconds, or within about less than 2 seconds.

The porous body of irradiated oxidized cellulose that forms the implant can further, according to some embodiments, hold and retain a quantity (measured in either mass or volume) of biocompatible fluid in the second hydrated state that is greater than the dry mass of the implant in the first rigid state. The amount of hydration that the implant can achieve in transitioning from the first rigid state to the second hydrated state can be measured by its Water Holding Capacity (WHC) value. The WHC value will be explained in detail further below, but generally is a measurement of the mass of the biocompatible fluid the implant in its second hydrated state retains relative to the dry mass of the implant in its first rigid state. The higher the WHC value is, the greater the ability of the implant to take up biocompatible fluids. Without being bound to any particular theory, it is believed that the ability of the implant to take up a sufficiently large quantity of fluid, relative to its dry weight size, can have a direct correlation to the implant surface's ability to conform to both regular and irregular anatomical surfaces and secondary medical device surfaces. According to one embodiment, the implant has a WHC of at least about 7.0, where the oxidizing agent has a concentration of 0.3M or greater. According to another embodiment, the ratio of the WHC value of the implant to its surface area (measured in square centimeters) is at least about 2.7:1.

The implant has a variable range of degradation profiles that can be manipulated to align with the clinical indication for which it is intended to be implanted. For example, when the implant is selected for use as a dural replacement patch, the porous body that forms the implant can have a degradation profile that substantially matches the natural tissue replacement rate of native dura mater. In vitro degradation testing, done under conditions simulating an in vivo environment, can be done to evaluate an implant's degradation profile with respect to a desired clinical indication, for example, as a dura replacement or a hemostat. In vitro testing can be conducted for any length of time as is desired, for example, one day, one week, four weeks, two months, six months, one year, or multiple years. According to one embodiment, the porous body has a one week in vitro degradation profile (as explained in further detail below) under simulated body fluid (SBF) conditions in the range of about zero to about 90 percent. According to another embodiment, the porous body has a one week in vitro degradation profile in the range of about zero to 40 percent, when the oxidizing agent has a concentration of approximately 0.1M. According to yet another embodiment, the porous body has a one week in vitro degradation profile in the range of about 20 to 90 percent, when the oxidizing agent has a concentration of approximately 0.3M. According to still another embodiment, the porous body has a one week in vitro degradation profile in the range of about zero to 60 percent, when the porous body has been oxidized for at least one hour. According to a further embodiment, the porous body has a one week in vitro degradation profile in the range of about 15 to 80 percent, when the porous body has been oxidized for at least three hours. In certain preferred embodiments the porous body has an in vitro degradation rate, measured over four weeks, of about 80% to about 100%.

According to a further embodiment of the disclosure, the implant can be a scaffold or carrier for one or more active agents. The active agent or agents can be impregnated within the porous body of cellulose that forms the implant, coated onto a surface of the implant, and/or both. According to one embodiment, the active agent or agents can be impregnated within and/or coated onto the implant substantially at or near the time of implantation (i.e., intraoperatively). In an alternative embodiment, the active agent or agents can be impregnated within and/or coated onto the implant prior to the time of implantation (i.e., preoperatively). In certain embodiments, more than one active agent can be impregnated within and/or coated onto the implant, and further the more than one active agents can be impregnated within and/or coated onto the implant at different time periods. For example, some active agents can be preoperatively combined with the implant, while other active agents can be combined intraoperatively. Active agents that can be utilized with the implant include any compositions suitable for treatment at the anatomical location, such as, bone marrow, autograft, osteoinductive small molecules, osteogenic material, stem cells, bone morphogenic proteins, antibacterial agents, calcium phosphate ceramics, and mixtures and blends thereof.

The present disclosure further describes a method of producing a body of oxidized cellulose that is porous and resorbable including (a) irradiating a body of cellulose so as to form an irradiated body of cellulose, and (b) reacting the irradiated body of cellulose with an oxidizing agent so as to form a body of oxidized cellulose.

The body of oxidized cellulose formed can be, according to one embodiment, porous, non-pyrogenic, and resorbable.

According to one embodiment the method can further include the step of partially dehydrating the body of irradiated cellulose, preferably by mechanically pressing the cellulose body. According to another embodiment, the method can further include the step of at least partially dehydrating the body of oxidized cellulose, preferably by critical point drying using supercritical carbon dioxide. According to a further embodiment, the method can include contacting the non-pyrogenic body of cellulose, the irradiated body of cellulose, and/or the body of oxidized cellulose with one or more active agents.

Any suitable oxidizing agent can be used in reacting with the irradiated body of cellulose according to the present method. Some examples of suitable oxidizing agents can include metaperiodate, hypochlorite, dichromate, peroxide, permanganate or nitrogen dioxide. A preferred oxidizing agent is sodium metaperiodate. According to one embodiment of the method, the cellulose and metaperiodate react in a molar ratio range of 1:1 to about 1:160 of cellulose to metaperiodate, and in another embodiment, the cellulose and metaperiodate react in a molar ratio range of 1:1 to about 1:120 of cellulose to metaperiodate. In a preferred embodiment, the cellulose and metaperiodate react in a molar ratio of about 1:120 of cellulose to metaperiodate. The molar concentration range of the oxidizing agent can vary as desired. According to one embodiment of the method, the oxidizing agent has a concentration range of about 0.05M to about 1.0M in the reaction, and in another embodiment, the oxidizing agent has a concentration range of about 0.1M to about 0.4M in the reaction. Likewise the reaction time between the irradiated body of cellulose and the oxidizing agent can vary as desired. According to one embodiment of the method, the oxidizing agent and the cellulose react for about 0.1 hours to about 72 hours, and in another embodiment, the oxidizing agent and the cellulose react for about 3 hours to about 12 hours. For example, at or near a reaction temperature of 40° C., the oxidizing agent can react with the cellulose at a concentration and time range of about 0.1M for about 5 hours, to about 0.5M for about 12 hours. Preferably, the oxidizing agent can be present in a concentration range of about 0.2M to about 0.4M for about 5 hours.

Reacting the irradiated body of cellulose with an oxidizing agent to form a body of oxidized cellulose according to the methods of the present disclosure can yield a variable degree of oxidation. According to one embodiment of the method, the body of oxidized cellulose has a degree of oxidation of at least about 25% after one hour of reacting between the oxidizing agent and the cellulose. According to another embodiment, the body of oxidized cellulose has a degree of oxidation of at least about 40% after two hours of reacting between the oxidizing agent and the cellulose. And in a further embodiment, the body of oxidized cellulose has a degree of oxidation of at least about 45% after two hours of reacting between the oxidizing agent and the cellulose. In certain embodiments, bodies of oxidized cellulose formed according to the embodiments of the method described herein have a degree of oxidation in the range of about 20% to about 70%.

According to one embodiment of the present disclosure a method or methods of production can be utilized in the following manner.

Preparation of the Cellulose Body

In preparing the resorbable biomaterial of the disclosure, *Gluconacetobacter xylinus* (*Acetobacter xylinum*) cells are cultured (incubated) in a bioreactor containing a liquid nutrient medium at about 30° C. at an initial pH of about 4.1-4.5. Cellulose production can be achieved using, for example, sucrose as a carbon source, ammonium salts as a nitrogen source, and corn steep liquor as nutrient source. The fermentation process is typically carried out in a shallow bioreactor with a lid which reduces evaporation. Such systems are able to provide oxygen-limiting conditions that help ensure formation of a uniform cellulose membrane. Dimensions of the bioreactor can vary depending on the desired shape, size, thickness and yield of the cellulose being synthesized.

The main fermentation process, following the incubation step, is typically carried out under stationary conditions for a period of about 8-120 hours, preferably 24-72 hours, during which the bacteria in the culture medium synthesize and deposit thin layers of cellulose sheets containing the microorganisms, thus forming a cellulose membrane. Depending on the desired thickness and/or cellulose yield, the fermentation can be stopped, at which point the membrane can be harvested from the bioreactor. According to one embodiment, the main fermentation is stopped after a relatively short period to yield a uniform, low cellulose content membrane (pellicle). The excess medium contained in the pellicle is then removed by standard separation techniques such as compression or centrifugation, which results in a partially dehydrated pellicle.

Cellulose Body Purification

The partially dehydrated cellulose pellicle can then be subject to a purification processing that renders the cellulose nonpyrogenic. According to one embodiment the purification method is a chemical purification of the cellulose membrane. The cellulose is subjected to a series of caustic (e.g., concentrated sodium hydroxide) chemical wash steps to convert the cellulose membrane into a nonpyrogenic material, followed by soaking and/or rinsing with filtered water, until a neutral pH is achieved. Alternatively, or in conjunction with these steps, a short soak in diluted acetic acid can also be conducted to ensure neutralization of the remaining sodium hydroxide. Purification processes using various exposure times, concentrations and temperatures, as well as mechanical techniques including pressing, can be utilized on the unpurified cellulose membrane. Processing times in sodium hydroxide of about 1 to about 12 hours have been studied in conjunction with temperature variations of about 30° C. to about 100° C. to optimize the process. A preferred or recommended temperature processing occurs at or near 70° C.

The amount of endotoxins left in the cellulose body after processing may be measured by Limulus Amebocyte Lysate (LAL) test. The cleaning process described herein is capable of providing a nonpyrogenic cellulose membrane (<0.06 EU/ml), which meets the FDA requirements for dura substitute materials. Following the purification of the cellulose membrane, according to one embodiment, the pellicle can be mechanically compressed to a desired weight and thickness.

Irradiation of the Cellulose Body

According to the disclosure, the non-pyrogenic cellulose membrane is irradiated with ionizing radiation. According to one embodiment, the radiation is γ-radiation. The cellulose membrane can absorb transmitted radiation in a range of about 10 kGy to about 100 kGy, and more preferably about 20 kGy to about 40 kGy. In a particular embodiment, the cellulose membrane can absorb transmitted γ-radiation in a range of about 20 kGy to about 26.5 kGy. In one embodiment of the disclosure the radiation is provided in a single exposure or dosage. In an alternative embodiment, the radiation can be provided through more than one exposure. For example, the cellulose body according the disclosure can be irradiated once, twice, or three times according to the disclosure. Further, where more than one dosage or exposure is applied to the cellulose body, the radiation transmitted and absorbed by the cellulose body for each of the multiple dosages can be of varying ranges. It should be appreciated by one skilled in the art that the number of exposures and the intensity of the radiation can be varied as desired.

In addition to irradiation, the cellulose membrane may be presoaked in an electrolyte solution in order to promote a more uniform oxidation and increase the rate of oxidation. The electrolyte may be from the sulfate or chloride series, preferably NaCl. The electrolyte concentration may be in the range from about 0.001M to about 1.0M, preferably about 0.05M to about 0.1M, and more preferably about 0.2M to about 0.4M. The presoak may last in the range of 30 minutes to 1 month, preferably 10 hours to 24 hours.

Oxidation of the Irradiated Cellulose Body

Following the irradiation and optional presoak steps, the cellulose membrane is then reacted with a suitable oxidizing agent, which could include, for example, chromic acid, hypochlorite, dichromate, nitrogen dioxide, nitrogen tetroxide, or sodium metaperiodate. According to one embodiment, the oxidizing agent is sodium metaperiodate. It should be noted that when selecting metaperiodate, the reaction is preferably conducted in the dark. According to one embodiment, the oxidation reaction with the oxidizing agent is for a time period in the range of about 30 minutes to 72 hours, preferably about 2-16 hours, and more preferably about 2-6 hours. The oxidation reaction can typically proceed at a temperature range of 18° C. to 60° C., preferably 30° C. to 50° C., and more preferably at about 40° C. According to another embodiment, the oxidation reaction with the oxidizing agent is for a time period of at least about one hour, and in yet another embodiment for at least about 3 hours. The container(s) are placed on a shaker and agitated at 20-500 rpm, preferably 350-450 rpm. The molar ratio between cellulose and metaperiodate can be maintained at the range of 1:1-1:160, preferably 1:1-1:120, and more preferably at about 1:120. Upon completion of the oxidation reaction, the oxidized cellulose membrane can be washed multiple times in filtered water on an ice-bath to remove excess metaperiodate. Alternatively, it can be washed in ethylene glycol to neutralize metaperiodate followed by multiple rinses in DI water.

In an addition to, or alternatively to the oxidation process previously described, prior to oxidation, the cellulose membrane can be ground up to form a slurry and then homogenized into a fine suspension of cellulose fibers. The homogenized suspension is then oxidized with sodium metaperiodate as described previously. An oxidized cellulose suspension is then recovered and washed to remove the excess of metaperiodate. The suspension is then placed in a mold and cross-linked to form a stable oxidized cellulose membrane again.

In yet another alternative embodiment, the cellulose membrane can undergo critical point drying prior to being oxidized. Critical point drying is a stepwise process wherein water in the cellulose membrane is exchanged with a non-aqueous solvent that is soluble with water, for example ethanol. The ethanol is then displaced with liquid carbon dioxide. This drying process can enhance the penetration of the oxidizing agent into the cellulose membrane. The dried membrane is reacted with the oxidizing agent, as described above, and recovered and washed in a manner as described above.

Drying of the Cellulose Body Using Supercritical Carbon Dioxide

Following any of the oxidation processes described above, the cellulose membrane can be further dried by critical point drying utilizing supercritical carbon dioxide. As previously explained above, the water in the cellulose membrane is exchanged with a non-aqueous solvent (e.g., ethanol). The solvent is then replaced with liquid carbon dioxide through a process called critical point drying. During critical point drying, the cellulose membranes are loaded onto a holder, sandwiched between stainless steel mesh plates, and then soaked in a chamber containing supercritical carbon dioxide under pressure. The holder is designed to allow the $CO_2$ to circulate through the cellulose membrane while mesh plates stabilize the membrane to prevent the membrane from waving during the drying process. Once all of the organic solvent has been removed (which in most typical cases is in the range of about 1-6 hours), the liquid $CO_2$ temperature is increased above the critical temperature for carbon dioxide so that the $CO_2$ forms a supercritical fluid/gas. Due to the fact that no surface tension exists during such transition, the resulting product is a dried membrane which maintains its shape, thickness and 3-D nanostructure. The dried product undergoes cutting, packaging and sterilization.

EXAMPLES

Unless otherwise stated herein, irradiated cellulose used in the examples below was irradiated in a range of about 20-26.5 kGy.

Unless otherwise stated herein, native cellulose used in the examples had a similar cellulose content (measured in g/cm$^2$) as the oxidized celluloses (both irradiated and non-irradiated) prior to their undergoing either irradiation and/or oxidation.

Percent Oxidation of Samples

The percentage of oxidized cellulose in a cellulose membrane was determined by measuring the amount of aldehyde content present. For example, the oxidized samples were reacted with 10 ml 0.05M NaOH at 70° C. for 15-25 minutes in a stirred beaker. The suspension was then cooled to room temperature and 10 ml of 0.05M HCl was added to neutralize NaOH. The excess of acid was titrated with 0.01M NaOH using phenolphthalein as an indicator. The following formula was used to calculate the oxidation percentage of the cellulose sample:

$$\text{Oxidation \%} = [(M_{NaOH\ Tit} * V_{NaOH\ Tit} * MW_{oxidized\ cellulose} / M_{oxidized\ cellulose}) * 100]/2$$

TABLE 1

| | |
|---|---|
| $M_{NaOH\ Tit}$ | Molarity of NaOH used for titration w/ phenolphthalein indicator |
| $V_{NaOH\ Tit}$ | Volume of NaOH used in titration step |
| $MW_{oxidized\ cellulose}$ | Molecular weight of oxidized cellulose (162 g/mol) |
| $M_{oxidized\ cellulose}$ | Mass in grams of oxidized cellulose sample |
| 100 | Used to covert to percentage |
| 2 | To account for dialdehyde nature of oxidized cellulose |

Figure 3:
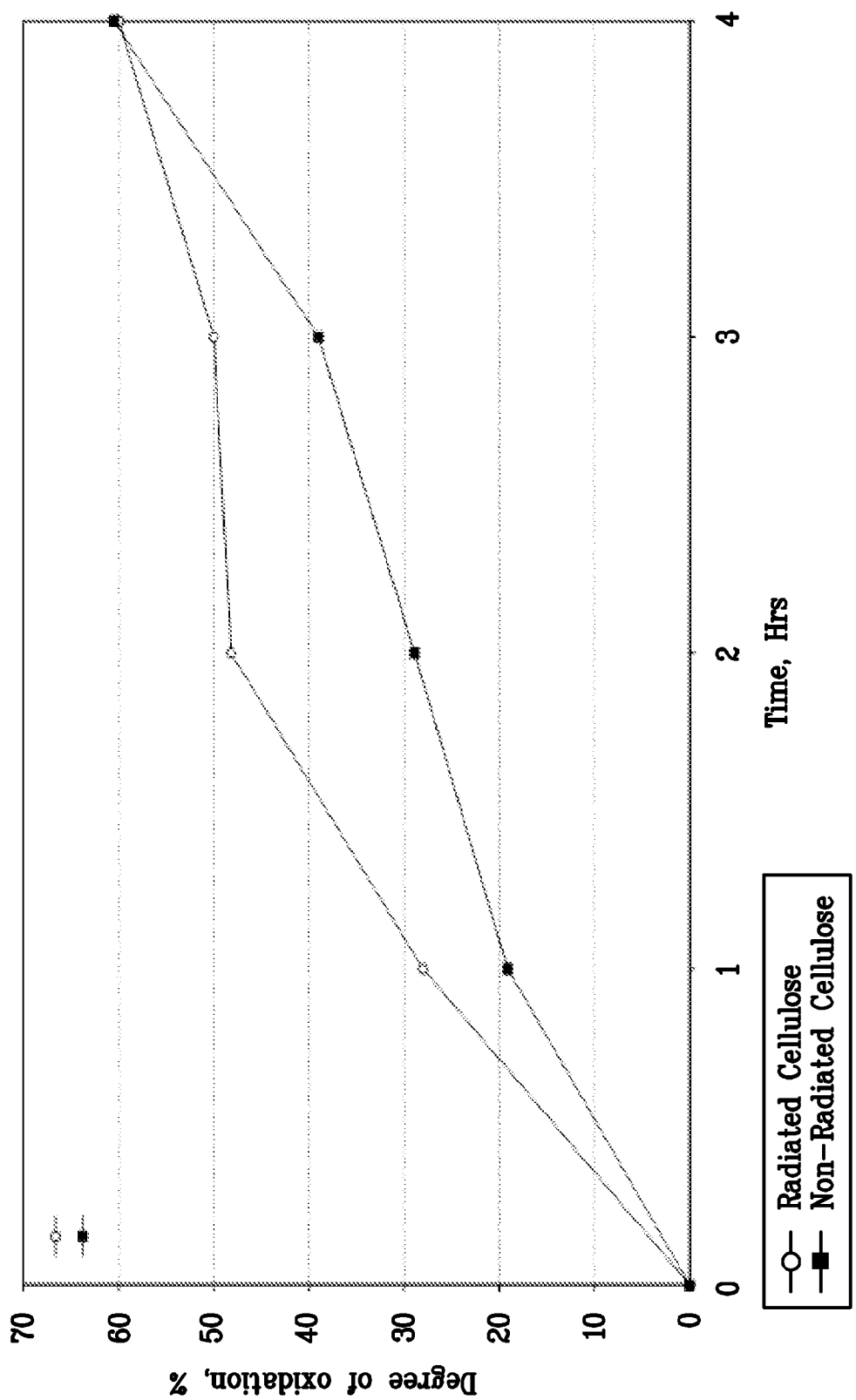
FIG. 3 is a graphical representation of degree of oxidation for both an irradiated oxidized cellulose according to the present disclosure and a non-irradiated oxidized cellulose.

FIG. 3 is a graphical representation displaying the degree of oxidation calculated according to the methodology described above for both an irradiated oxidized cellulose according to the present disclosure and a non-irradiated oxidized cellulose. Sodium periodate was used as the oxidizing agent at a constant concentration of 0.3M and constant temperature of 40° C. Percentage of oxidation was measured in samples over a time period of 0-4 hours.

Conformability Testing

Conformability was tested by rehydrating dehydrated cellulose samples in a solution of SBF (pH=7.4) and testing its ability to conform to irregularities on the anatomically correct surface of a cranial pulsation model (Synthes, Inc.). Dry oxidized implant samples (both irradiated and non-radiated), oxidized at 0.3M periodate, 40° C., 3 hrs, were placed on the moist surface of the cranial pulsation model and rinsed with SBF. A conformable sample was defined as: 1) displaying rapid rehydration (transition from the first rigid state to second hydrated state), for example, within 30 seconds, within 20 seconds, within 10 seconds, and preferably within 5 seconds; 2) complete attachment to the surface of the model; and 3) adherence to the surface during simulated pulsation for up to 1 minute.

The cranial pulsation model used is shown and described in WD Losquadro et al., "Polylactide-co-glycolide Fiber-Reinforced Calcium Phosphate Bone Cement," Arch Facial Plast Surg, 11(2), March/April 2009, pp. 105-106. The pulsation model was designed and manufactured by Synthes, Inc. The model consisted of 6 anatomically correct adult skulls having various diameter openings that simulated cranial defects. The skulls were made from solid foam polyurethane and dura mater made from silicone. Each skull was attached to an individual water pump with water sealed from the external environment and the water from the pump capable of being forced into the interior of the simulated dura mater material to mimic dural pulsations.

To simulate a surgical wound environment, the skull model was housed in a closed water bath maintained at a constant 37° C. and 95%-100% relative humidity using a circulating water heater. Water within the bath reached the base of the model skulls but did not bathe the defect area. The closed water pump was programmed to simulate intraoperative observations of dura pulsation displacement of about 1.7 mm to 2.0 mm.

Burst Strength Testing

Oxidized cellulose samples of various sizes were tested for ball burst strength using a manual burst tester, made by Synthes, USA and calibrated at 11.4 kg (25 lbs.). The testing methodology used to measure burst strength was based upon the procedures described ASTM D2207-00 (Reapproved 2010), "Standard Test Method for Bursting Strength of Leather by the Ball Method." The dry samples are rehydrated in the SBF for 5 minutes and then sandwiched in a stainless steel holder containing a central opening of 1 inch diameter. The test method is designed to measure the bursting strength of the sample by measuring the force required to force a spherical ended plunger through the oxidized cellulose membrane; that is, the plunger is used to penetrate the samples until failure while force is measured digitally.

Cellulose Content Measurement

Samples with known surface area were air dried in the oven at 55° C. overnight. Cellulose content was measured by dividing the weight of the dried sample by its surface area and was expressed in $g/cm^2$.

Figure 4:
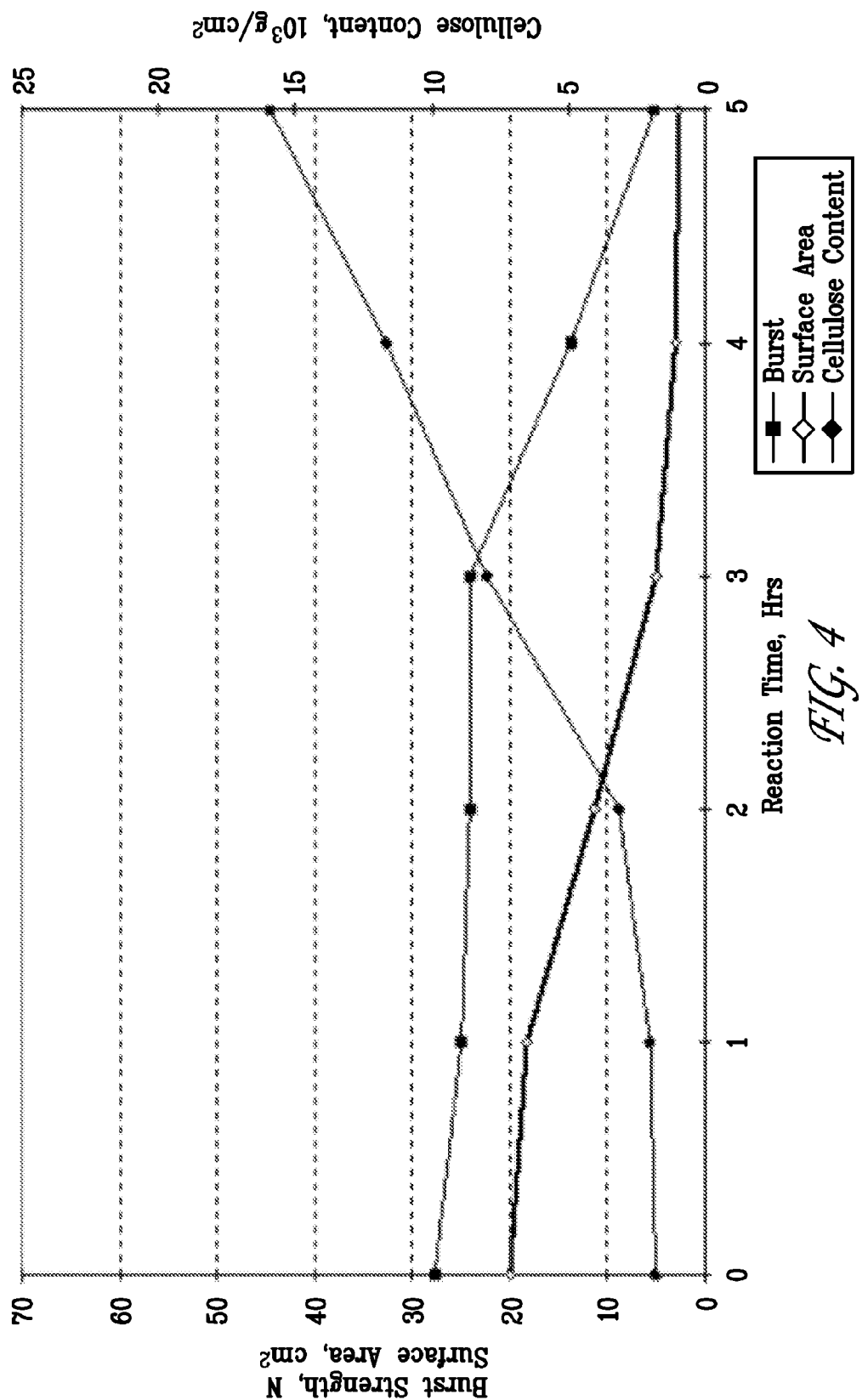
FIG. 4 is a graphical representation of burst strength, cellulose content and surface area for an irradiated oxidized cellulose according to the disclosure.
Figure 5:
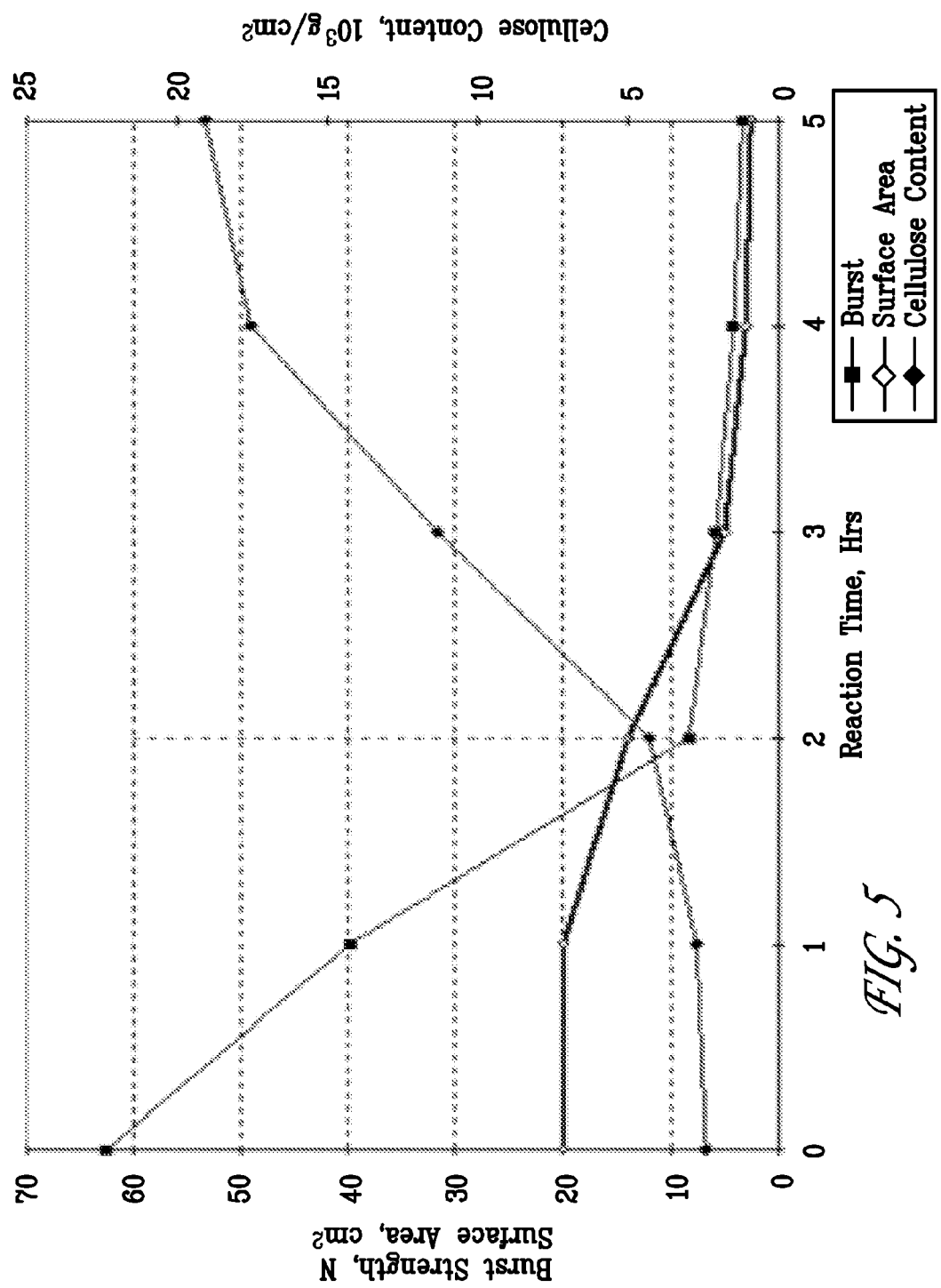
FIG. 5 is a graphical representation of burst strength, cellulose content and surface area for a non-irradiated oxidized cellulose sample.

Data relating to the above experiments including cellulose content, surface area, burst strength and conformability for an irradiated oxidized cellulose sample and a non-irradiated oxidized cellulose sample are graphically depicted in FIGS. 4 and 5, respectively. The samples were oxidized with sodium metaperiodate at a constant concentration of 0.3M at 40° C. over a time range of about 0-5 hours. The irradiated oxidized samples tested and depicted in FIG. 4 were conformable when rehydrated at all values as measured according to the standards as previously described for conformability. In contrast, the non-irradiated oxidized samples tested and depicted in FIG. 5 were conformable when rehydrated only within values to the left of the dashed vertical line, i.e., at an oxidation time of less than 2 hours.

SEM Observations

Figure 6A:
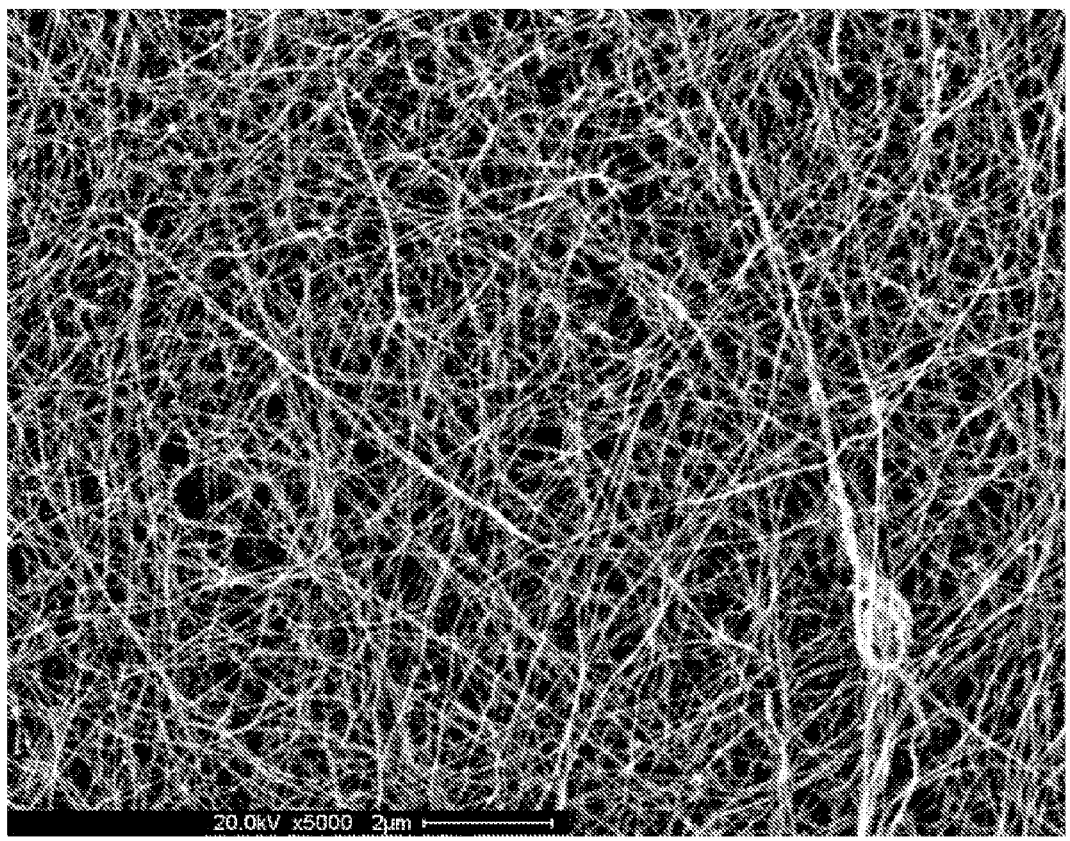
FIGS. 6A-6C are SEM images for samples of native cellulose, non-radiated oxidized cellulose, and an irradiated oxidized cellulose according to the present disclosure, respectively
Figure 6B:
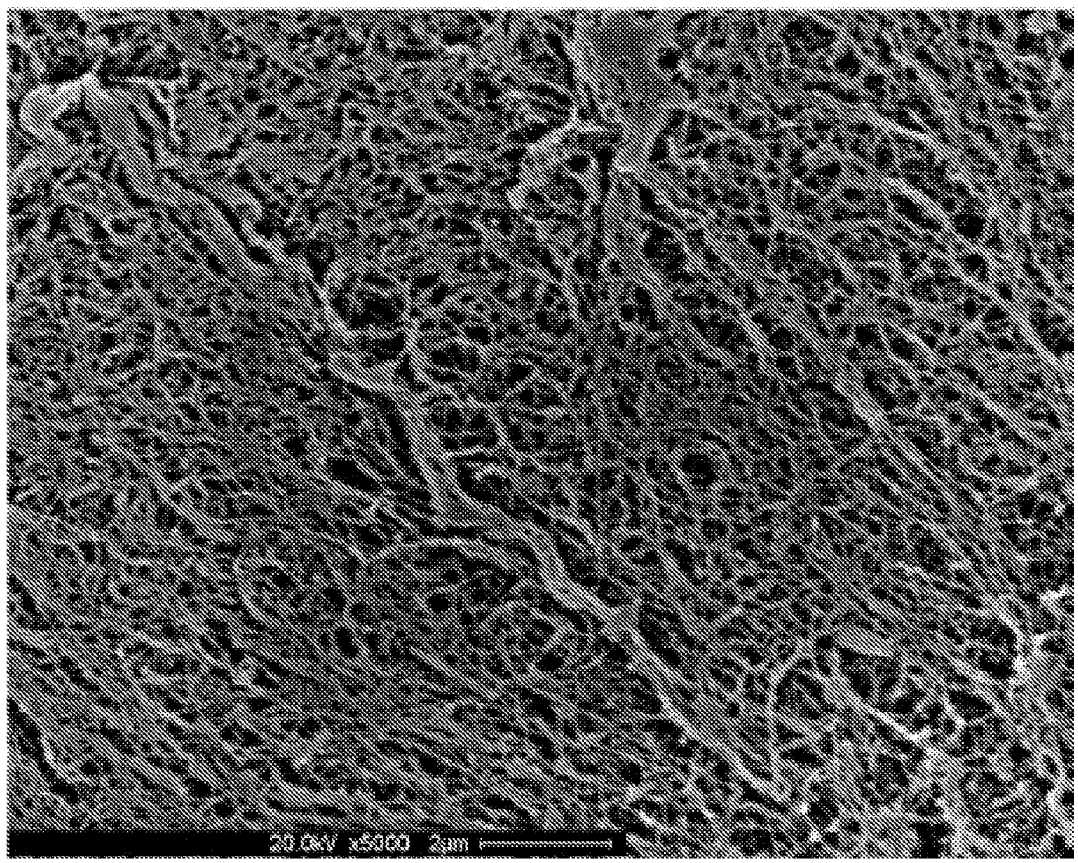
Figure 6C:
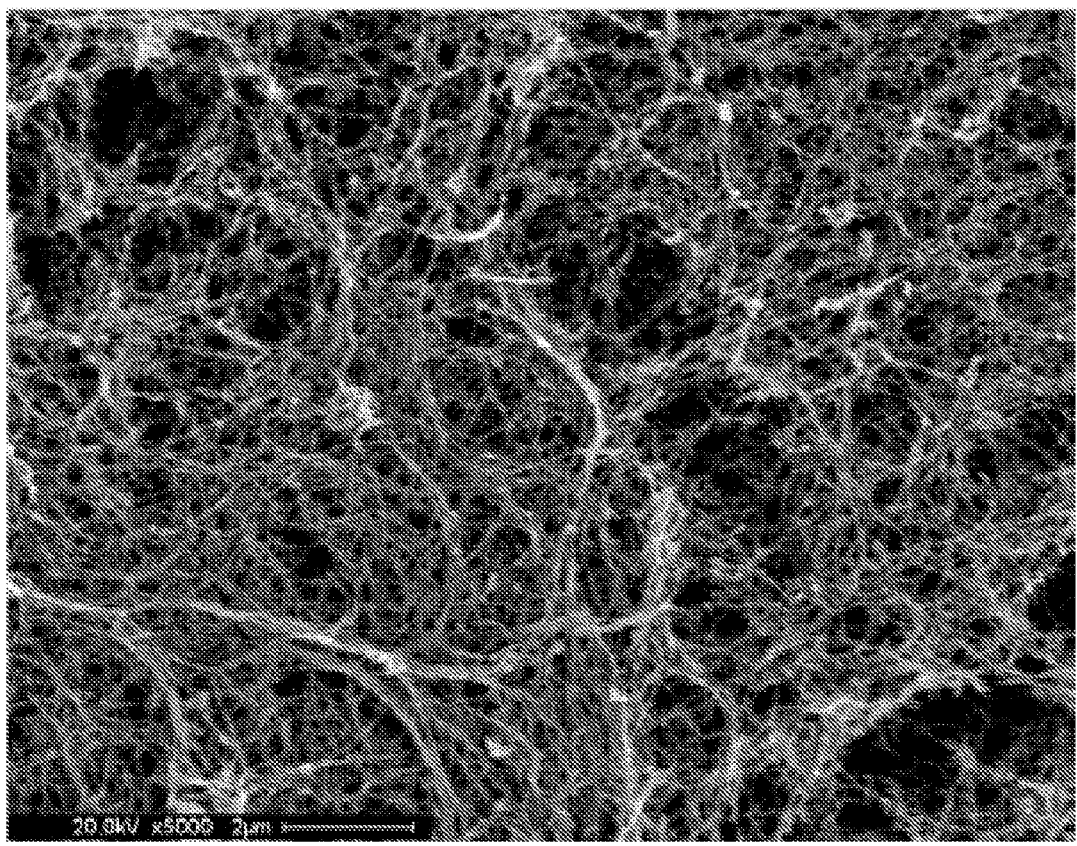

Samples of cellulose membranes including native cellulose, non-irradiated oxidized cellulose and irradiated oxidized cellulose were dried with supercritical $CO_2$ and then coated with gold. Oxidation was carried out at 0.3M periodate, 40° C., 3 hrs. A Hitachi field emission scanning electron microscope operating at 20 kV was used for examinations of the samples. FIGS. 6A-6C are SEM images of samples of native cellulose, non-radiated oxidized cellulose, and radiated oxidized cellulose samples, respectively. The SEM images show that native cellulose, as shown in FIG. 6A have a fibrillar, 3-dimensionally oriented and ordered structure of cellulose chains. The non-radiated oxidized cellulose, as shown in FIG. 6B, is a more compact structure than the native cellulose, with regions of larger fibrils stacked together. The radiated oxidized sample, as shown in FIG. 6C, is less ordered generally than the previous cellulose samples, having a more chaotic structure with generally smaller fibrils and generally higher incidence of heterogenic regions than the other cellulose samples.

X-ray Diffraction (XRD) Testing

Figure 7A:
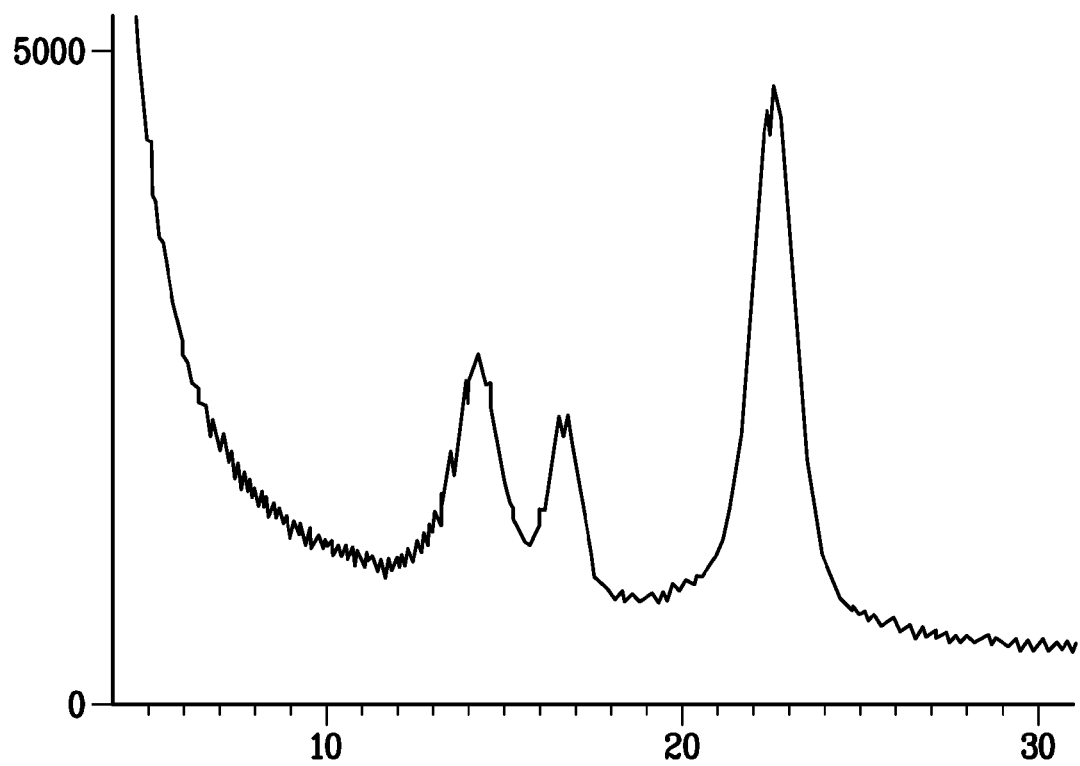
FIGS. 7A-7C are XRD images for samples of native cellulose, non-radiated oxidized cellulose, and an irradiated oxidized cellulose according to the disclosure, respectively.
Figure 7B:
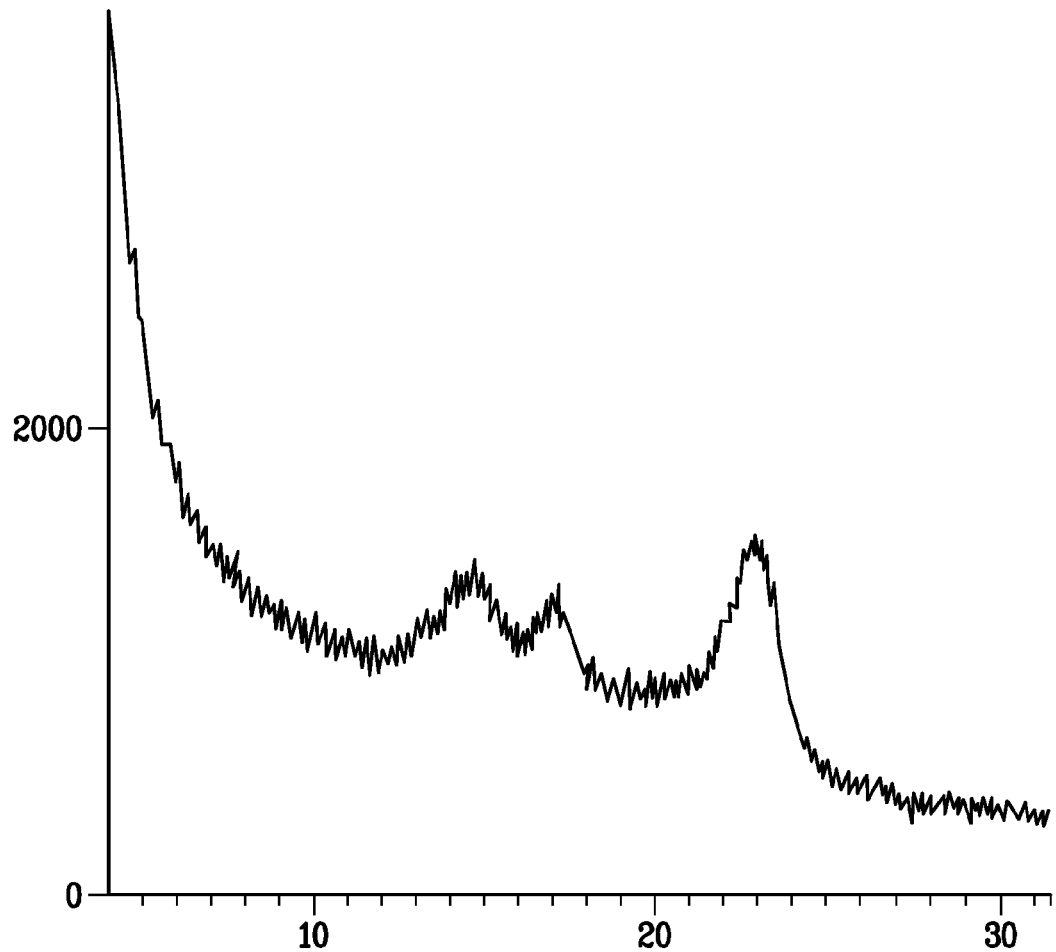
Figure 7C:
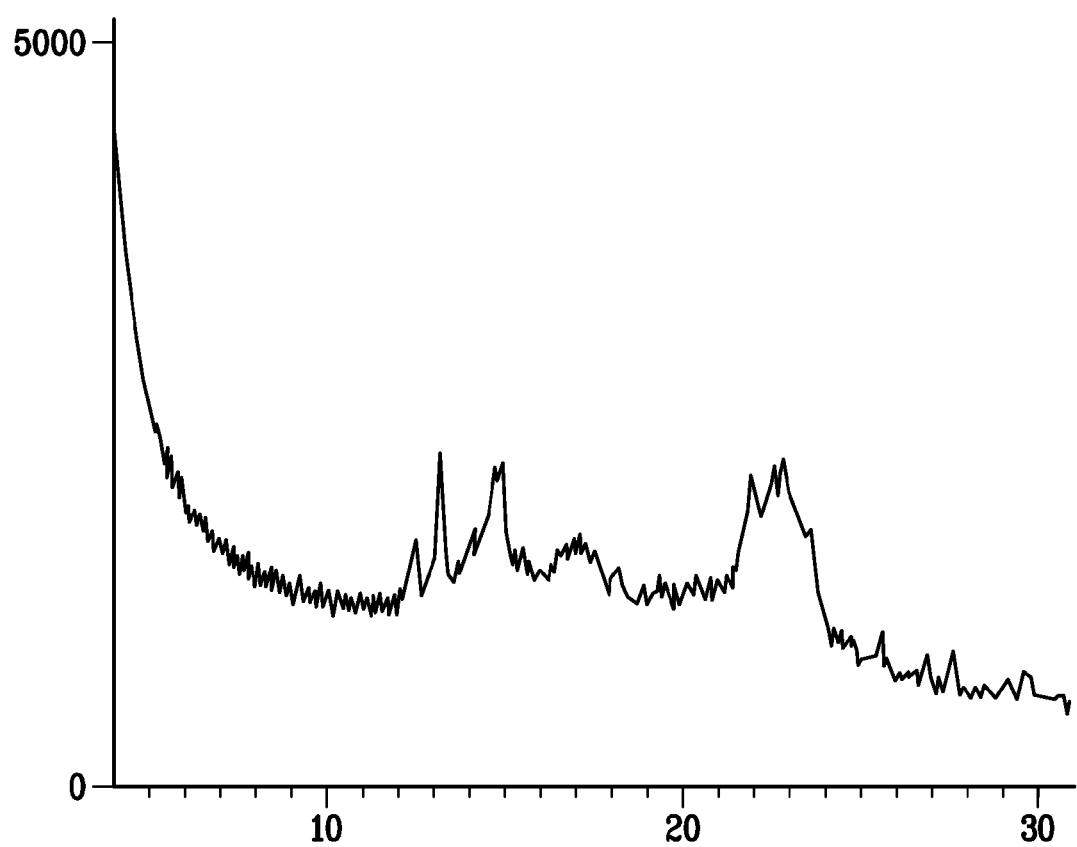

Dried cellulose membrane samples, including native, non-irradiated oxidized, and irradiated oxidized samples, were placed in XRD sample cup holders, placed into the XRD magazine and then into the device for measurement. Oxidation was carried out at 0.3M periodate, 40° C., 3 hrs. X-ray diffraction spectra were recorded using Ni filtered Cu-Kα radiation produced by the PANalytical XRD System. Scans were performed over the 4-90° 2θ range, but analyzed from 4-40° 2θ range. The data were analyzed with the HighScore Plus XRD software. FIGS. 7A-7C are XRD spectrographs of the native, non-irradiated oxidized, and irradiated oxidized samples, respectively. As can be seen in the XRD displays, the native sample, FIG. 7A, has a highly ordered crystalline structure, followed by the non-radiated cellulose sample, FIG. 7B, with the irradiated sample, FIG. 7C showing the least ordered crystalline structure.

Percent crystallinity was calculated using the following equation:

$$CrI = 100 \times [(I_{002} - I_{Amorph})/I_{002}],$$

where CrI is the degree of crystallinity, $I_{002}$ is the maximum intensity of the (002) lattice diffraction (22° 2θ) and $I_{Amorph}$ is the intensity diffraction at 18° 2θ. Table 2 below shows the measured crystallinity indexes for the measured cellulose samples.

TABLE 2

| Cellulose sample | CrI [%] |
| --- | --- |
| Native | 81.9 |
| Nonradiated oxidized | 36.3 |
| Irradiated oxidized | 35.3 |

Rehydration/Water Holding Capacity Measurement

For this experiment, both irradiated and non-radiated bodies of cellulose were cut into 4 cm×5 cm samples. These samples were subjected to periodate solutions for oxidation at 40° C. and the following conditions:

| Periodate Molarity (M) | Time (Hours) |
| --- | --- |
| 0.1 | 3 |
| 0.1 | 5 |
| 0.2 | 4 |
| 0.3 | 3 |
| 0.3 | 4 |
| 0.3 | 5 |
| 0.4 | 3 |
| 0.4 | 4 |

-continued

| Periodate Molarity (M) | Time (Hours) |
|---|---|
| 0.4 | 5 |
| 0.4 | 6 |

Reactions of both the irradiated and non-radiated cellulose samples were done in duplicate. After each reaction was completed, the samples were prepared for testing by washing and $CO_2$ drying according to the methods previously disclosed herein.

Next, initial weight and surface area dimensions of all samples were obtained, measuring non-radiated samples against their irradiated counterpart. With a petri dish prepared with 20 ml SBF, a non-radiated sample of cellulose was placed into the fluid for 30 seconds and then weighed out. This hydration step was then repeated for the irradiated sample. Hydration for 30 seconds and then weighing out wet mass was repeated for all samples prepared. The water holding capacity (WHC) for each condition was calculated with the following equation:

$$\frac{\text{Wet mass (g)}}{\text{Dry Mass (g)}} = WHC$$

Averages of the WHC were taken to measure the difference between non-radiated and irradiated cellulose in rehydration capabilities. Also measured was the relationship between WHC and surface area (SA) for each sample. Table 3 below shows the individual sample results for each sample of radiated oxidized cellulose and non-radiated oxidized cellulose at the given oxidation parameters. Table 4 provides a summary of the average WHC and WHC/SA values for each of the radiated and non-radiated oxidized samples at the given oxidation parameters.

TABLE 3

| Sample | Conditions | Dry Mass (g) | Surface Area (cm2) | Wet Mass (g) | WHC | Average WHC | WHC/Surface Area (SA) | Avg. (WHC/SA) |
|---|---|---|---|---|---|---|---|---|
| 0.1M/3 Hrs | Radiated | 0.0357 | 13.02 | 1.0740 | 30.08 | 30.08 | 2.311 | 2.311 |
| 0.1M/3 Hrs | Non-Radiated | 0.0639 | 18.62 | 0.9750 | 15.26 | 15.26 | 0.819 | 0.819 |
| 0.1M/5 Hrs | Radiated | 0.0323 | 12.3 | 0.6970 | 21.58 | 21.58 | 1.754 | 1.754 |
| 0.1M/5 Hrs | Non-Radiated | 0.0643 | 13.26 | 0.9690 | 15.07 | 15.07 | 1.136 | 1.136 |
| 0.2M/4 Hrs | Radiated | 0.0281 | 6.16 | 0.4240 | 15.09 | 15.09 | 2.450 | 2.450 |
| 0.2M/4 Hrs | Non-Radiated | 0.0429 | 6.16 | 0.4580 | 10.68 | 10.68 | 1.733 | 1.733 |
| 0.3M/3 Hrs | Radiated | 0.0248 | 4.56 | 0.4040 | 16.29 | 14.12 | 3.572 | 3.085 |
| 0.3M/3 Hrs | Radiated | 0.0251 | 4.6 | 0.3000 | 11.95 | | 2.598 | |
| 0.3M/3 Hrs | Non-Radiated | 0.0507 | 3.57 | 0.3470 | 6.84 | 7.02 | 1.917 | 1.965 |
| 0.3M/3 Hrs | Non-Radiated | 0.0423 | 3.57 | 0.3040 | 7.19 | | 2.013 | |
| 0.3M/4 Hrs | Radiated | 0.0240 | 2.55 | 0.2350 | 9.79 | 9.06 | 3.840 | 3.382 |
| 0.3M/4 Hrs | Radiated | 0.0270 | 2.85 | 0.2250 | 8.33 | | 2.924 | |
| 0.3M/4 Hrs | Non-Radiated | 0.0604 | 2.52 | 0.2690 | 4.45 | 4.91 | 1.767 | 1.826 |
| 0.3M/4 Hrs | Non-Radiated | 0.0590 | 2.85 | 0.3170 | 5.37 | | 1.885 | |
| 0.3M/5 Hrs | Radiated | 0.0197 | 2.21 | 0.1660 | 8.43 | 8.69 | 3.813 | 4.058 |
| 0.3M/5 Hrs | Radiated | 0.0225 | 2.08 | 0.2014 | 8.95 | | 4.303 | |
| 0.3M/5 Hrs | Non-Radiated | 0.0560 | 2.08 | 0.1990 | 3.55 | 3.49 | 1.708 | 1.732 |
| 0.3M/5 Hrs | Non-Radiated | 0.0555 | 1.95 | 0.1900 | 3.42 | | 1.756 | |
| 0.4M/3 Hrs | Radiated | 0.0196 | 3 | 0.1830 | 9.34 | 9.62 | 3.112 | 3.207 |
| 0.4M/3 Hrs | Radiated | 0.0212 | 3 | 0.2100 | 9.91 | | 3.302 | |
| 0.4M/3 Hrs | Non-Radiated | 0.0577 | 2.38 | 0.2510 | 4.35 | 4.16 | 1.828 | 1.888 |
| 0.4M/3 Hrs | Non-Radiated | 0.0511 | 2.04 | 0.2030 | 3.97 | | 1.947 | |
| 0.4M/4 Hrs | Radiated | 0.015 | 1.8 | 0.1000 | 6.67 | 8.74 | 3.704 | 5.366 |
| 0.4M/4 Hrs | Radiated | 0.0175 | 1.54 | 0.1894 | 10.82 | | 7.028 | |
| 0.4M/4 Hrs | Non-Radiated | 0.0453 | 1.95 | 0.1940 | 4.28 | 3.94 | 2.196 | 2.189 |
| 0.4M/4 Hrs | Non-Radiated | 0.0425 | 1.65 | 0.1530 | 3.60 | | 2.182 | |
| 0.4M/5 Hrs | Radiated | 0.0170 | 1.3 | 0.1230 | 7.24 | 7.69 | 5.566 | 5.497 |
| 0.4M/5 Hrs | Radiated | 0.0140 | 1.5 | 0.1140 | 8.14 | | 5.429 | |
| 0.4M/5 Hrs | Non-Radiated | 0.0326 | 1.3 | 0.1100 | 3.37 | 3.24 | 2.596 | 2.476 |
| 0.4M/5 Hrs | Non-Radiated | 0.0360 | 1.32 | 0.1120 | 3.11 | | 2.357 | |
| 0.4M/6 Hrs | Radiated | 0.0112 | 1.2 | 0.1160 | 10.36 | 9.49 | 8.631 | 7.904 |
| 0.4M/6 Hrs | Radiated | 0.0137 | 1.2 | 0.1180 | 8.61 | | 7.178 | |
| 0.4M/6 Hrs | Non-Radiated | 0.0418 | 0.9 | 0.1170 | 2.80 | 2.52 | 3.110 | 2.577 |
| 0.4M/6 Hrs | Non-Radiated | 0.0307 | 1.1 | 0.0690 | 2.25 | | 2.043 | |

TABLE 4

| | Avg. WHC | | Avg. (WHC/SA) | |
|---|---|---|---|---|
| Oxid. Values | Radiated | Non-Radiated | Radiated | Non-Radiated |
| 0.1M/3 Hrs | 30.08 | 15.26 | 2.3106 | 0.8195 |
| 0.1M/5 Hrs | 21.58 | 15.07 | 1.7544 | 1.1365 |
| 0.2M/4 Hrs | 15.09 | 10.68 | 2.4495 | 1.7331 |
| 0.3M/3 Hrs | 14.12 | 7.02 | 3.0854 | 1.9651 |
| 0.3M/4 Hrs | 9.06 | 4.91 | 3.3819 | 1.8263 |
| 0.3M/5 Hrs | 8.69 | 3.49 | 4.0581 | 1.7320 |
| 0.4M/3 Hrs | 9.62 | 4.16 | 3.2071 | 1.8876 |
| 0.4M/4 Hrs | 8.74 | 3.94 | 5.3658 | 2.1890 |
| 0.4M/5 Hrs | 7.69 | 3.24 | 5.4971 | 2.4762 |
| 0.4M/6 Hrs | 9.49 | 2.52 | 7.9043 | 2.5766 |

In vitro Degradation Profile

Samples of both irradiated and non-irradiated oxidized cellulose having various degrees of oxidations, prepared according to the disclosure, were tested in vitro by incubation in SBF. Degradation profiles showed that the cellulose samples remained mechanically stable (in the form of a membrane/film) over at least a 2-4 week period. After that initial period, the samples began to disintegrate into irregular cellulosic masses and degrade over the following 1-3 months, leaving approximately 0.1%-5.0% of their initial dry mass.

Both real-time and accelerated studies were conducted. Samples of dried irradiated oxidized cellulose (approximately 1×1 cm squares) were placed in the sterile 50 ml centrifuge conical tubes filled with 20 ml of SBF (pH=7.4) and kept in static conditions at 37° C. or 55° C. for a period of time between 1 week and 6 months (real time). For the real-time study, the SBF in each tube was changed daily for 5 initial days and then weekly by centrifuging samples, decanting old SBF and replacing it with a fresh one. Samples were analyzed at 1, 2, 3, 4, 14, 28, 90 and 164 days. At each time point, tubes were centrifuged to collect the residual pellet. The supernatant was decanted and DI water was added to wash the pellet from residual SBF. The tubes were stirred briefly and centrifuged again to collect pellet. The DI water washing step was repeated twice. The pellet was then dried in the oven at 60° C. to constant weight. The percent of degradation was calculated as difference between the dry pellet weight and original sample weight.

Figure 8:
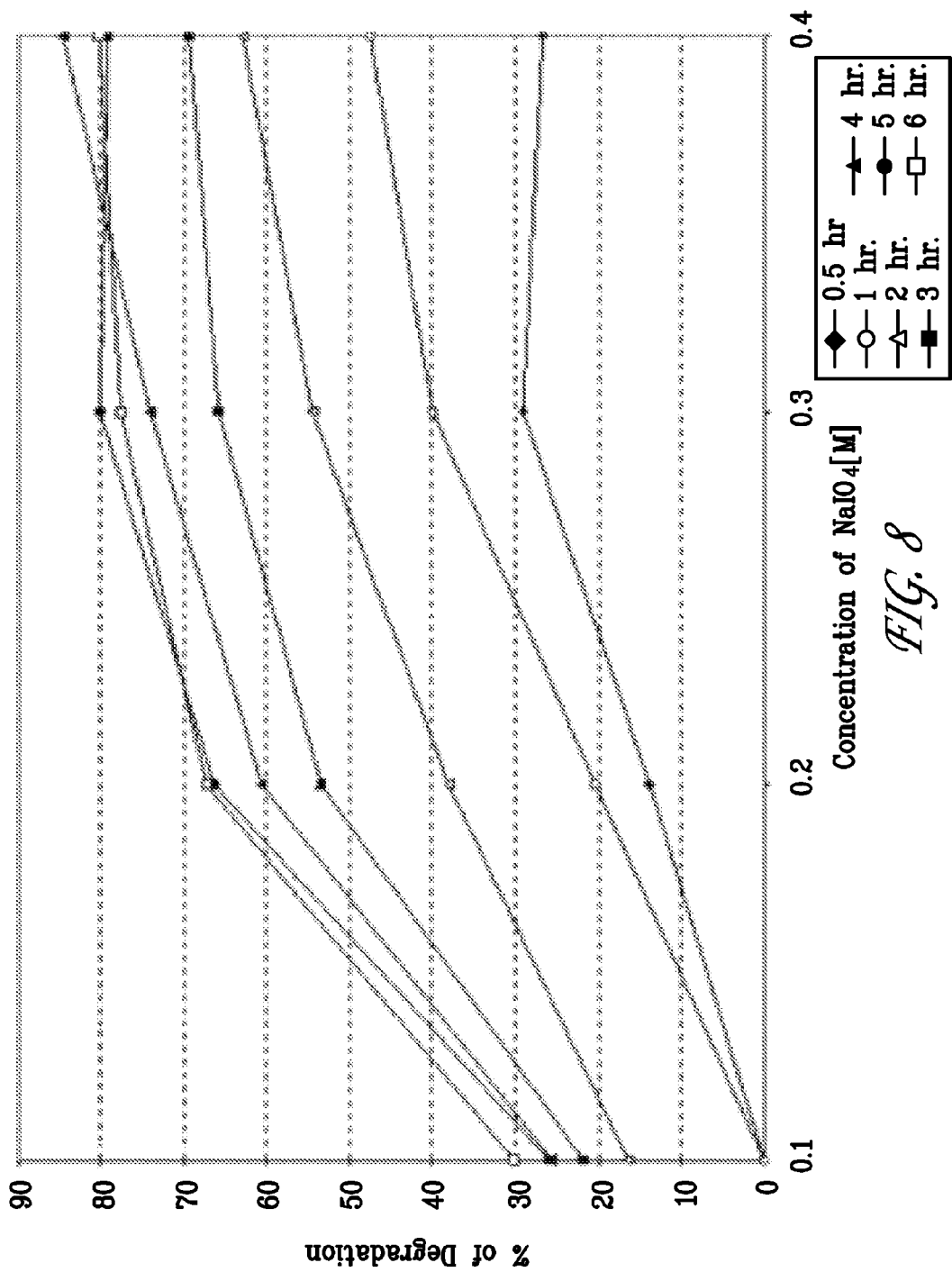
FIG. 8 is a graphical representation of a series of in vitro degradation profiles for irradiated oxidized cellulose according to the disclosure.
Figure 9:
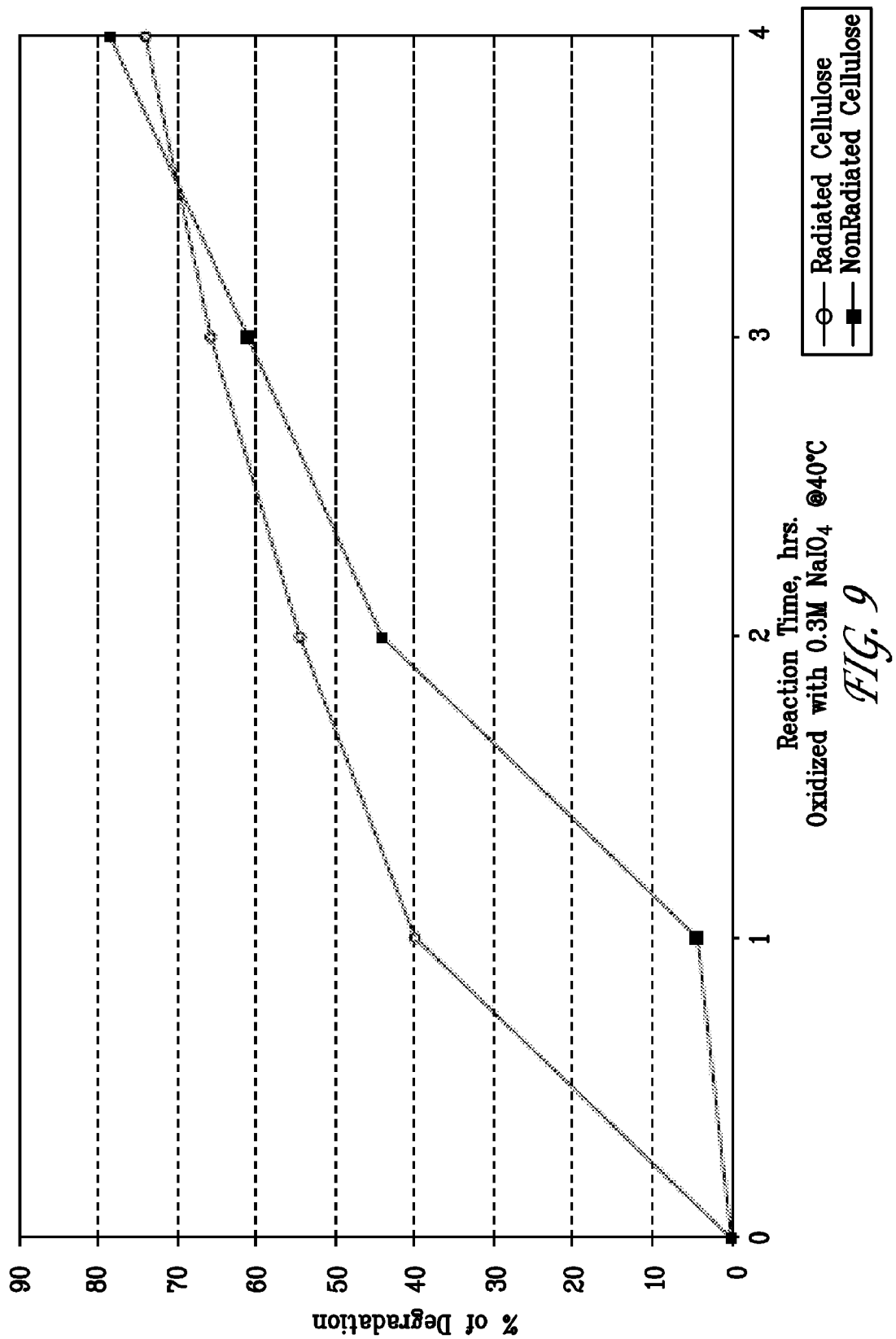
FIG. 9 is a graphical comparison of in vitro degradation profiles of a non-radiated oxidized cellulose and an irradiated oxidized cellulose according to the disclosure.

FIG. 8 graphically shows degradation profiles (SBF; pH=7.4, 55° C., 7 days) of irradiated cellulose, oxidized at different periodate concentrations. For all conditions tested, a progressive loss of the samples' dry mass was observed throughout the study. Once incubated in SBF, samples become softer, gel-like structures with a high degree of translucency. Depending on the oxidation conditions used, a degradation range of about 10-95% can be obtained after 7 days incubation time. The results show that degradation rate is related to oxidation degree, which can be controlled by periodate concentration, reaction temperature and reaction time. A conformable and mechanically stable biomaterial with desired degradation rate can be prepared by using such approach. FIG. 9 graphically depicts the results of the in vitro degradation (dry mass loss) for both irradiated and non-irradiated cellulose samples, oxidized for various periods of time (1-4 hours). The curves show that there was a weight loss in both types of samples oxidized for 3 and 4 hours. The initial rate of mass loss for samples oxidized for less than about 3 hours is greater? for the irradiated cellulose than the non-irradiated cellulose.

Samples of cellulose of the type used in the in vitro degradation were submitted to Polymer Solutions Incorporated (PSI) (Blacksburg, Va.) for analysis of molecular weight distributions using GPC with light scattering detection. Three types of samples were submitted: 1) a sample of native microbial cellulose, identified as "Native Cellulose (wet);" 2) a sample of irradiated oxidized microbial cellulose, identified as "Oxidized Cellulose (wet);" and 3) a residual sample of irradiated oxidized microbial cellulose that had been subjected to a seven day in vitro degradation process as described above, identified as "Implant Residual Content."

As used in this experiment, the term "wet" is used to indicate that the "Native Cellulose" sample and the "Oxidized Cellulose" sample did not undergo the step of critical point drying with supercritical $CO_2$ that was previously described. Both the "Oxidized Sample" and the "Implant Residual Content" sample were oxidized at 0.3M periodate, 40° C., 3 hrs.

The molecular weight distributions of the cellulose samples were analyzed using gel permeation chromatography (GPC) with light scattering detection. Approximately half of the 4×5 cm piece of Native Cellulose (wet) and the entire 2.2×3.0 cm piece of Oxidized Cellulose (wet) were placed in separate 40-mL glass scintillation vials. A piece of Whatman #1 filter paper was ground for about 5 minutes in a small blade-type coffee mill, and approximately 20 mg of the resulting "fluff" was weighed into a 40-mL scintillation vial.

The Whatman filter paper was included as a control for the dissolution process, and also for use in estimating the specific refractive index increment (dn/dc) of cellulose in DMAc. 10 mL of pure water and a disposable stir bar were added to each vial. Each vial was stirred for approximately 5 hours at 50° C. The Native Cellulose (wet) and Oxidized Cellulose (wet) samples did not disintegrate. Therefore, the wet cellulose pieces were placed in a small food processor with 60 to 70 mL of pure water and processed for 60 to 90 seconds, resulting in slurries of very small fibrous particles. The slurries were then vacuum filtered on 47-mm 0.2-µm nylon membranes, just until excess water was removed.

The wet cellulose samples were then transferred to Whatman Vecta-Spin centrifuge filters, which contained 10-µm polypropylene mesh filters. The water was centrifuged off and replaced with HPLC grade methanol and soaked overnight. The following day the methanol was spun off, and an additional 3-hour soak with fresh methanol was performed, followed by a 20-minute centrifugation. The solvent exchange process was then repeated using dried N,N-dimethylacetamide (DMAc) for 3 exchanges with soak times of 75 minutes, overnight, and 30 minutes, with 20 minutes centrifugation after each soak.

The DMAc-wet samples and Whatman filter paper control were then transferred into 40-mL scintillation vials. 20 mg of the Implant Residual Content sample was weighed into a 40-mL scintillation vial as well. To each of these, 2 mL of a solution of 8% lithium chloride in DMAc and a stir bar were added. The samples were stirred for 3 days at room temperature, and were then placed in a refrigerator at 4° C. for three additional days. The Native Cellulose and the Whatman filter paper control were completely dissolved. The Oxidized Cellulose sample formed a cloudy solution with numerous gel-like particles. The Implant Residual Content sample was mostly dissolved, but with a very small percentage of the original sample that would not dissolve.

The Native Cellulose and Oxidized Cellulose solutions were diluted with 14 mL of DMAc. The Whatman cellulose control and the Implant Residual Content sample were diluted with 30 mL of DMAc. The diluted solutions were stored at approximately 4° C. for an additional day before being filtered through 0.45-µm pore size PTFE syringe filters into GPC autosampler vials. Following filtration, duplicate GPC injections of each sample solution were performed under parameters listed in Table 5 below and molecular weights were calculated using dual-angle light scattering.

TABLE 5

| Parameter | Value |
| --- | --- |
| Mobile Phase: | 0.5% LiCL in DMAc |
| Columns: | (2) Tosoh Alpha M, 300 × 7.8 mm |
| Flow Rate: | 0.8 mL/min |
| Column Temperature: | 50° C. |
| Detectors: | Visotek Triple Detector Array (TDA) w/RI, 7° and 90° light scattering, & differential viscometer detectors |
| Dectector Temperature: | 50° C. |
| Injection Volume: | 200 µL |
| Mol. Wt. Calculation Method: | Dual-Angle Light Scattering |
| Light Scattering/RI Detection Wavelength: | 670 nm |
| dn/dc of cellulose: | 0.1309 mL/g* |

Figure 10:
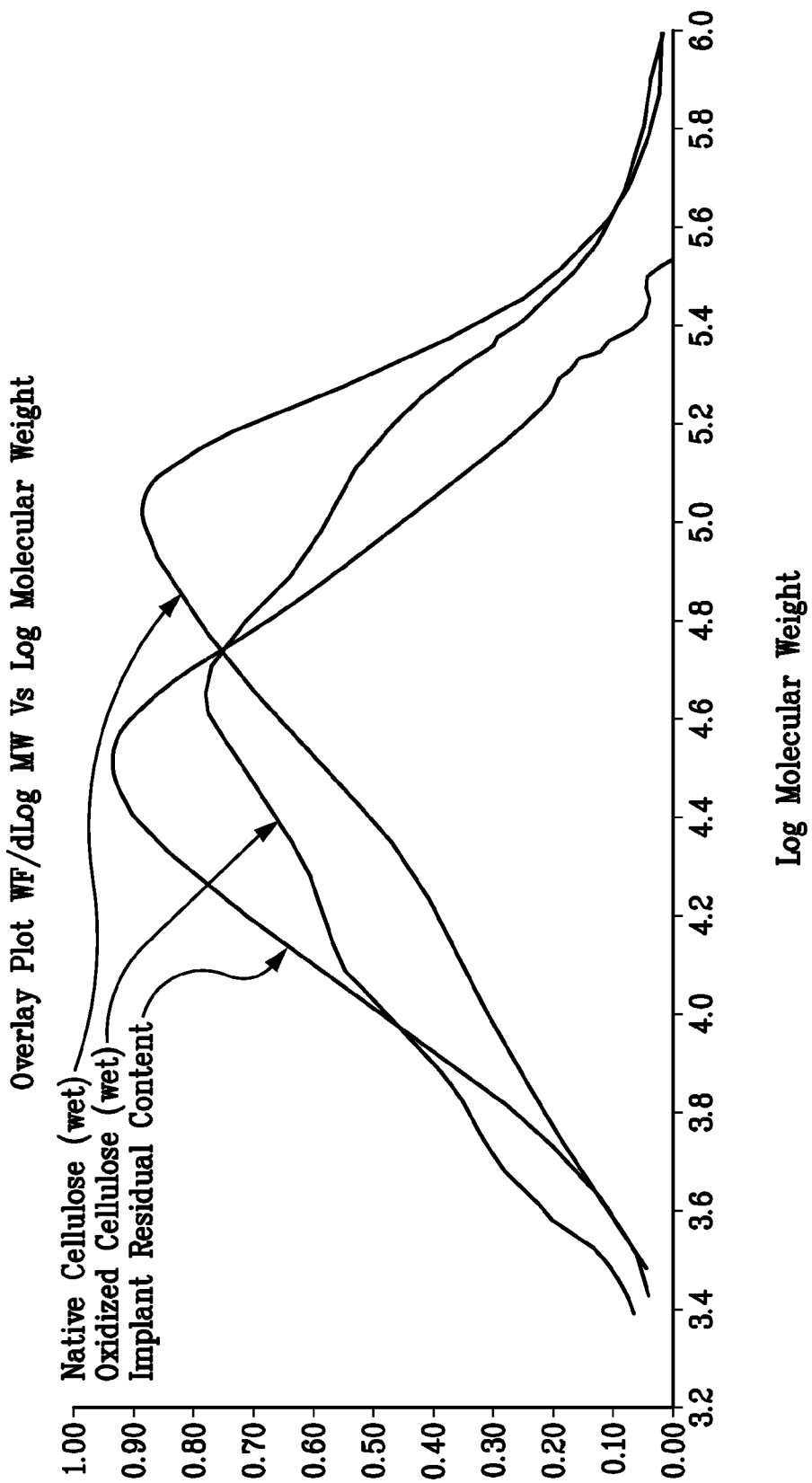
FIG. 10 is a graphical representation of molecular weight distributions for a native cellulose sample, an irradiated oxidized cellulose sample according to the disclosure, and a residual sample of an irradiated oxidized cellulose according to the disclosure after in vitro degradation testing.

*dn/dc of cellulose value refers to value of cotton cellulose used as control value The molecular weight averages (Mn, Mw, Mz) and polydispersity (Mw/Mn) are presented for duplicate injections of each sample in Table 6. The molecular weight distribution plots of all samples are compared and graphically depicted in FIG. 10. The specific refractive index increment (dn/dc) value of cellulose in DMAc, used for the light scattering molecular weight calculations, was estimated from the RI detector peak area for duplicate injections of the Whatman filter paper control. The bacterial cellulose samples were assumed to have the same dn/dc value as the Whatman filter paper (cotton cellulose).

TABLE 6

| Sample | GPC Run | $M_n$ (g/mol) | $M_w$ (g/mol) | $M_z$ (g/mol) | $M_w/M_n$ |
|---|---|---|---|---|---|
| Native | 1 | 27,047 | 87,951 | 187,092 | 3.25 |
| Cellulose | 2 | 26,383 | 88,598 | 194,792 | 3.36 |
| (wet) | Average | 26,715 | 88,275 | 190,942 | 3.30 |
|  | Std. Dev. | 470 | 457 | 5,445 | 0.08 |
| Oxid. | 1 | 22,598 | 75,899 | 216,679 | 3.36 |
| Cellulose | 2 | 22,633 | 76,687 | 248,783 | 3.39 |
| (wet) | Average | 22,616 | 76,293 | 232,731 | 3.37 |
|  | Std. Dev. | 25 | 557 | 22,701 | 0.02 |
| Implant | 1 | 17,134 | 43,602 | 89,334 | 2.54 |
| Residual | 2 | 21,227 | 46,578 | 93,085 | 2.19 |
| Content | Average | 19,181 | 45,090 | 91,210 | 2.37 |
|  | Std. Dev. | 2,894 | 2,104 | 2,652 | 0.25 |
| Whatman #1 | 1 | 289,819 | 476,627 | 678,373 | 1.64 |
| Filter Paper | 2 | 295,673 | 472,848 | 680,254 | 1.60 |
| (Control) | Average | 292,746 | 474,738 | 679,314 | 1.62 |
|  | Std. Dev. | 4,139 | 2,672 | 1,330 | 0.03 |

Radiation Dosage and in vitro Degradation

Four cellulose bodies were subjected to varying radiation dosages and then oxidized at 0.3M periodate, 40° C., 3 hrs. After undergoing oxidation, the samples' in vitro degradation rate (7 days) was measured.

Figure 11:
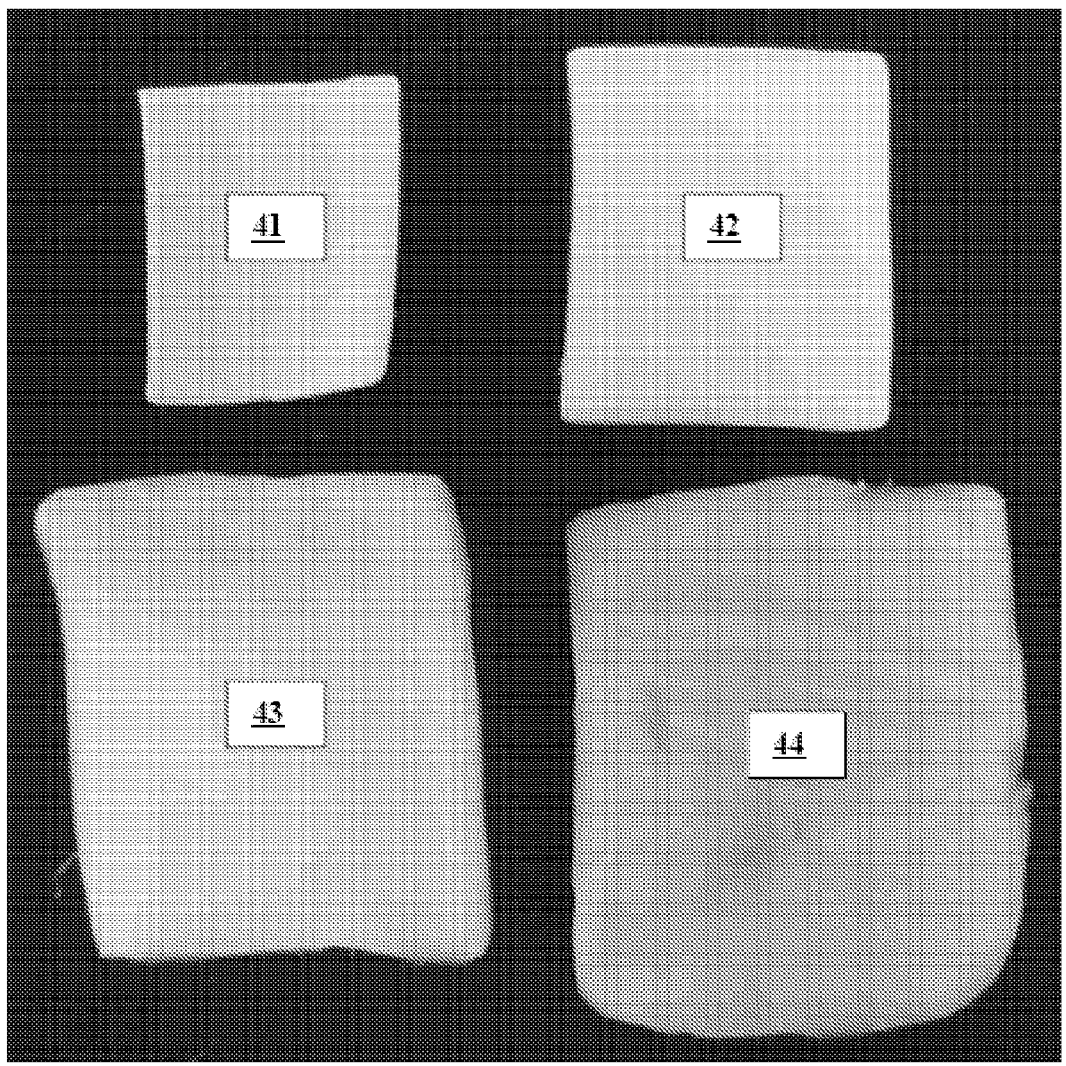
FIG. 11 is a top view photo of four oxidized cellulose samples subjected to different levels of radiation.

The cellulose bodies were sent to Sterigenics (Charlotte, N.C.) to undergo radiation exposure at various dosages. The samples were irradiated with gamma radiation using the ExCell® system, a high-precision, low-volume irradiator. Each exposure of radiation was intended to irradiate the samples in the range of about 20 kGy to about 26.5 kGy. Actual dosage levels for each treatment were measured to be about 23 kGy. Afterwards, the samples were oxidized using 0.3M periodate at 40° C. for three hours. FIG. 11 is a top view of the four samples after radiation exposure and subsequent oxidation. Sample 1, 41, was not radiated. Sample 2, 42, was exposed to one treatment at a dose of 23 kGy. Sample 3, 43, was exposed to two separate treatments, each at a dose of 23 kGy. Sample 4, 44, was exposed to three separate treatments, each at a dose of 23 kGy. The samples were measured for in vitro degradation, as previously described, for one week at SBF conditions at 55° C. Table 7 shows the measured percent of sample degradation of each sample after one week at SBF conditions, along with the sample weight, surface area, and cellulose content, prior to the start of the in vitro degradation test.

TABLE 7

| Sample | Degradation (7 days) | Weight (g) | Surface Area (cm²) | Cellulose Content ($10^3$ g/cm²) |
|---|---|---|---|---|
| Non-radiated | 71% | 0.0522 | 2.7 | 19.3 |
| Single radiated | 71% | 0.0629 | 3.6 | 17.0 |
| Double radiated | 70% | 0.0222 | 5.5 | 4.0 |
| Triple radiated | 71% | 0.0202 | 7.2 | 2.8 |

While increased radiation may affect the dry weight and size of the samples after oxidation, as shown in FIG. 11, there is not a corresponding change in overall degradation, as can been seen in Table 7. Without being bound by any particular theory, it is believed that radiation likely caused two things to occur in the tested samples: (1) chain scission occurred due to the formation of free radicals, which lowered the average molecular weight of the cellulose and (2) the free radicals promoted cross linking in the cellulose structure. Therefore, while chain scission is likely the dominant mechanism, the formation of small cross-linked molecules of varying geometries is also likely, which may prevent further degradation from occurring.

Again, without being bound by any particular theory, it is believed that the lowering of the molecular weight of the cellulose samples from increased exposure to radiation can cause an increased size of the oxidized cellulose samples as shown in FIG. 11. Further, any chain scission that occurs as a result of radiation decreases the length of cellulose chains, which prevents the sample from shrinking during oxidation. Non-radiated cellulose samples with longer chain lengths are likely affected by the oxidization procedure.

In vivo Studies

The in vivo study evaluated in vivo degradation rate and safety/biocompatibility of four irradiated oxidized cellulose implants according to the present disclosure (identified as TD 1-TD 4), each having a different oxidation profile, and compared them to 1) a commercially available cross-linked bovine tendon collagen, identified as CD 1, and 2) a native microbial cellulose, identified as CD 2. The oxidation profiles of the four implants according to the disclosure were as follows: TD 1 having a 55% oxidation profile, oxidized at 0.4M periodate, 40° C., 3 hrs.; TD 2 having a 84% oxidation profile, oxidized at 0.4M periodate, 40° C., 4 hrs.; TD 3 having a 50% oxidation profile, oxidized at 0.3M periodate, 40° C., 3 hrs.; and TD 4 having a 94% oxidation profile, oxidized at 0.3M periodate, 40° C., 5 hrs. All TD samples used in the in vivo studies were irradiated prior to oxidation according to the process described herein.

Seventeen male New Zealand White rabbits, (16 study animals plus 1 spare, per study protocol) were entered into the study. The 16 study animals were assigned to one of four groups of four animals each. The implants were all implanted by subcutaneous implantation in a rabbit model and evaluated at 2, 4, 12 and 26 weeks after implantation. Each animal received one of each of the six materials, implanted into separate subcutaneous pockets on the rabbit's back (three on each side of the dorsal midline). The location of each different implant in each rabbit was randomized according to a predetermined implantation matrix. The superficial fascia was bluntly dissected away from the underlying tissue to create a subcutaneous pocket deep enough to contain the test or control device (native microbial cellulose and resorbable collagen). After each test device or control device had been positioned, a pair of small skin staples were used to mark the location of the device and placed at the two corners of the test or control device closest to the incision site, but not associated with the material. A pair of 4-0 Prolene sutures was used to tack down the implant to the underlying subcutaneous tissue in order to prevent implant migration after implantation.

Four rabbits were euthanized and subjected to a limited necropsy at each of four different time points: 2 weeks, 4 weeks, 12 weeks or 26 weeks after implantation surgery. Necropsy was limited to gross observations of the implantation sites and peri-implant tissues, with limited tissue collection (consisting of collection from the operative sites of the implant surrounded by peri-implant tissues). The degradation of the implants at each site for each measurement period (2 weeks, 4 weeks, 12 weeks or 26 weeks) was recorded and is shown below in Tables 8-12, respectively.

TABLE 8

Week 2

| Terminal Assessment[a] | TD1 2 weeks | TD2 2 weeks | TD3 2 weeks | TD4 2 weeks | CD1 2 weeks | CD2 2 weeks |
|---|---|---|---|---|---|---|
| Inflammation[b] | 0.75 | 1.25 | 0.75 | 0.50 | 0.00 | 0.00 |
| Infection[b] | 0.00 | 0.00 | 0.00 | 0.00 | 0.00 | 0.00 |
| Fibrosis[b] | 0.00 | 0.00 | 0.00 | 0.25 | 0.00 | 0.00 |
| Seroma[b] | 0.00 | 0.25 | 0.00 | 0.00 | 0.00 | 0.00 |
| Hematoma[b] | 0.00 | 0.00 | 0.00 | 0.00 | 0.00 | 0.00 |
| Gross Vascularization[b] | 1.25 | 1.00 | 0.50 | 0.75 | 0.00 | 0.00 |
| Presence of Implant[c] | 1.00 | 1.00 | 1.00 | 1.00 | 0.25 | 0.00 |
| Implant Degradation[d] | 2.50 | 2.50 | 2.50 | 2.75 | 0.25 | 0.00 |
| Implant Measurement[e] | 27.0 | 65.3 | 25.0 | 47.0 | 91.8 | 145.0 |
| % of Original Implant Area Remaining | 17.3 | 41.8 | 25.0 | 37.6 | 58.7 | 92.8 |

TABLE 9

Week 4

| Terminal Assessment[a] | TD1 4 weeks | TD2 4 weeks | TD3 4 weeks | TD4 4 weeks | CD1 4 weeks | CD2 4 weeks |
|---|---|---|---|---|---|---|
| Inflammation[b] | 1.25 | 1.25 | 1.25 | 1.75 | 0.00 | 0.00 |
| Infection[b] | 0.00 | 0.00 | 0.00 | 0.00 | 0.00 | 0.00 |
| Fibrosis[b] | 0.00 | 0.00 | 0.00 | 0.00 | 0.00 | 0.00 |
| Seroma[b] | 0.00 | 0.00 | 0.00 | 0.00 | 0.00 | 0.00 |
| Hematoma[b] | 0.00 | 0.25 | 0.25 | 0.25 | 0.25 | 0.00 |
| Gross Vascularization[b] | 0.75 | 0.25 | 0.50 | 0.50 | 0.00 | 0.00 |
| Presence of Implant[c] | 1.00 | 1.00 | 1.00 | 1.00 | 0.50 | 0.00 |
| Implant Degradation[d] | 2.50 | 2.75 | 2.50 | 2.75 | 0.75 | 0.00 |
| Implant Measurement[e] | 15.5 | 17.8 | 11.0 | 29.5 | 49.5 | 94.0 |
| % of Original Implant Area Remaining | 9.9 | 11.4 | 11.0 | 23.6 | 31.7 | 60.1 |

TABLE 10

Week 12

| Terminal Assessment[a] | TD1 12 Weeks | TD2 12 Weeks | TD3 12 Weeks | TD4 12 Weeks | CD1 12 Weeks | CD2 12 Weeks |
|---|---|---|---|---|---|---|
| Inflammation[b] | 1.00 | 0.75 | 0.75 | 0.50 | 0.00 | 0.50 |
| Infection[b] | 0.00 | 0.00 | 0.00 | 0.00 | 0.00 | 0.00 |
| Fibrosis[b] | 0.00 | 0.00 | 0.25 | 0.00 | 0.00 | 0.50 |
| Seroma[b] | 0.00 | 0.00 | 0.00 | 0.00 | 0.00 | 0.00 |
| Hematoma[b] | 0.00 | 0.00 | 0.00 | 0.00 | 0.00 | 0.00 |
| Gross Vascularization[b] | 0.50 | 0.75 | 1.25 | 0.75 | 0.25 | 1.25 |
| Presence of Implant[c] | 1.00 | 1.00 | 1.00 | 1.00 | 1.75 | 0.00 |
| Implant Degradation[d] | 3.00 | 2.75 | 3.00 | 3.00 | 3.50 | 0.00 |
| Implant Measurement[e] | 7.0 | 47.3 | 30.0 | 42.0 | 9.5 | 120.8 |
| % of Original Implant Area Remaining | 4.5 | 30.2 | 30.0 | 33.6 | 6.1 | 77.3 |

TABLE 11

Week 26

| Terminal Assessment[a] | TD1 26 Weeks | TD2 26 Weeks | TD3 26 Weeks | TD4 26 Weeks | CD1 26 Weeks | CD2 26 Weeks |
|---|---|---|---|---|---|---|
| Inflammation[b] | 0.00 | 0.00 | 0.00 | 0.00 | 0.00 | 0.00 |
| Infection[b] | 0.00 | 0.00 | 0.00 | 0.00 | 0.00 | 0.00 |
| Fibrosis[b] | 0.25 | 0.25 | 0.38 | 0.25 | 0.00 | 0.38 |
| Seroma[b] | 0.00 | 0.00 | 0.00 | 0.00 | 0.00 | 0.00 |
| Hematoma[b] | 0.00 | 0.00 | 0.00 | 0.00 | 0.00 | 0.00 |
| Gross Vascularization[b] | 1.00 | 0.75 | 0.88 | 1.00 | 0.00 | 1.00 |
| Presence of Implant[c] | 1.25 | 1.25 | 1.25 | 1.50 | 2.00 | 1.00 |
| Implant Degradation[d] | 3.25 | 3.25 | 3.25 | 3.50 | 4.00 | 1.00 |
| Implant Measurement[e] | 5.8 | 19.0 | 22.5 | 0.0 | 0.0 | 53.5 |
| % of Original Implant Area Remaining | 3.7 | 12.2 | 22.5 | 0.0 | 0.0 | 34.2 |

[a]Average score.
[b]Scoring: 0 = None; 1 = Slight; 2 = Moderate; 3 = Severe
[c]Scoring: 0 = Material present as implanted; 1 = Material present, but signs of degradation; 2 = Material not present
[d]Scoring: 0 = Same as when implanted; 1 = Slight fragmentation; 2 = Moderate fragmentation; 3 = Severe fragmentation; 4 = Not able to score
[e]Implant measurement calculated in square millimeters (mm$^2$)

The control implants did not show any inflammation of note. After two weeks, there was some gross inflammation noted around all test material implants, with the least amount being around TD4. Inflammation increased slightly at all test material sites after four weeks, with the most inflammation being observed around TD4. At 12 weeks, inflammation at all sites was similar to that observed at two weeks, with the least amount observed around TD4. Inflammation was not observed around any of the implants at 26 weeks. No infection was observed at any time point. The TD2 implant site in one animal was noted to have a possible infection, but when examined microscopically, there was no evidence of infection, or evidence of bacterial colonies. There was little to no fibrosis observed grossly around any of the implants, except perhaps around the native microbial cellulose implant after 12 weeks. At 26 weeks, slight fibrosis was observed around all implants except at the cross-linked bovine tendon collagen sites because it was not present. There appeared to be a small seroma around the TD2 implant site in one animal at two weeks. No other sites at any time point contained a seroma.

One animal had evidence of a possible resolving hematoma near the TD2 implant site, and two animals had evidence of possible resolving hematomas associated with the TD4 implants, all after two weeks. These were likely caused by the surgical procedure itself. After four weeks, small hematomas were present in the CD 1 implant site in one rabbit, at the TD2 site in another animal, at the TD3 site in one animal and at the TD4 site in yet another animal. In all cases, these were likely a result of placement of the stay sutures. No hematomas were observed at either 12 or 26 weeks.

Gross vascularization (a sign of chronic inflammation) was also rarely observed at the early time points, but tended to increase at the 12 and 26-week time points, being greatest at the latter. It was most prominent around the TD 1 implant and least prominent around the TD3 implant at 2 weeks. No gross vascularization was observed around the control implants at 2 and 4 weeks, but it was evident after 12 weeks, especially around the native microbial cellulose implant. The cross-linked bovine tendon collagen and all test material implant sites also showed some gross vascularization after 12 weeks.

It was about equally present at all sites, except the cross-linked bovine tendon collagen sites, where it was not present at all at 26 weeks.

Figure 12A:
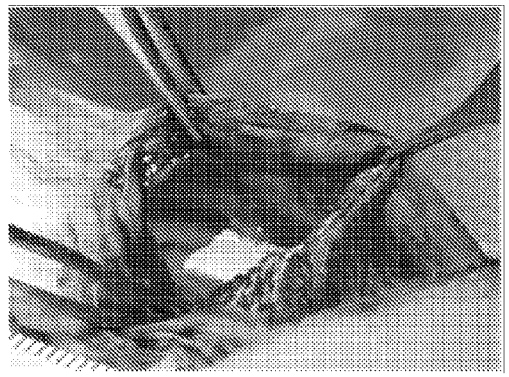
FIGS. 12A-F are photos of an irradiated oxidized cellulose sample of the disclosure taken at various time periods during an in vivo animal study.
Figure 12B:
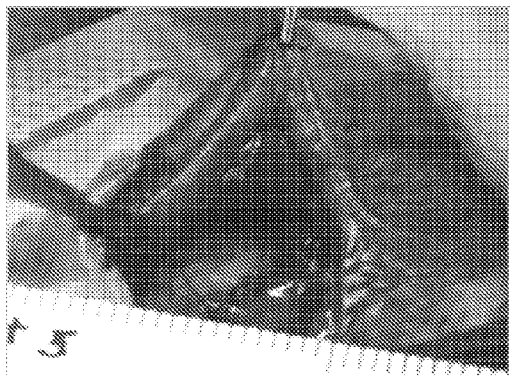
Figure 12C:
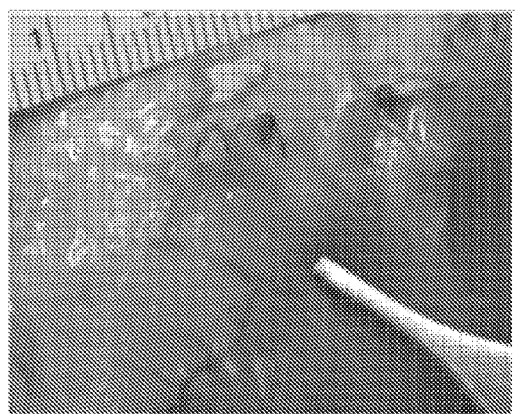
Figure 12D:
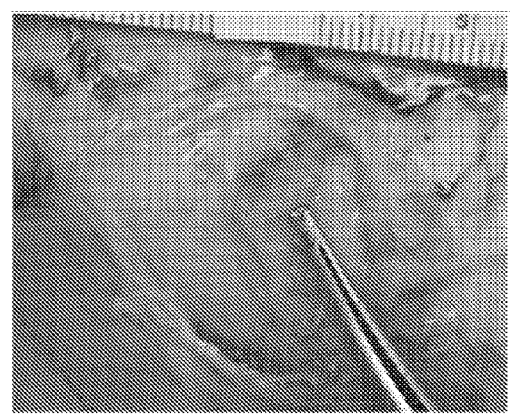
Figure 12E:
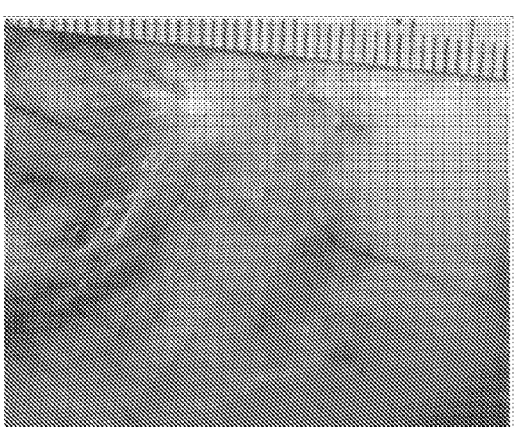
Figure 12F:
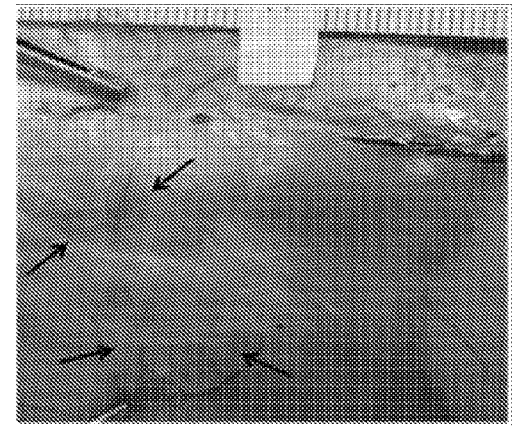

The representative necropsy images of test material TD1 are shown in FIGS. 12A-F. FIG. 12A shows an embodiment of the implant in a first rigid state immediately after placement in position in subcutaneous pocket. After placement, the implant rapidly transitioned to the second hydrated state by absorbing moisture from the surrounding tissue, and subsequently conformed and adhered to the tissue surface as shown in FIG. 12B. It should be noted that after hydration the implant displayed translucency and is nearly indistinguishable from the underlying tissue. FIG. 12C shows the implant 2 weeks after implantation where the implant was measurably thinner. FIG. 12D shows the implant 4 weeks after implantation where the implant was moderately degraded with one comparatively large piece remaining FIG. 12E shows the implant 12 weeks after implantation where the implant was severely degraded, there was discoloration of the tissue, and the portion of the degraded implant remaining was very diffuse and thin. FIG. 12F shows the implant 26 weeks after implantation where the implant was severely degraded; the portion of implant remaining was very diffuse and thin. Stay sutures are visible, and arrows indicate diffuse small areas of discoloration that may indicate fragments of remaining TD 1 implant material.

The native microbial cellulose implant showed no sign of degradation over the entire period of study. Cross-linked bovine tendon collagen on the other hand, showed some degradation at 2 weeks, was significantly degraded at 4 weeks, and was essentially not present at 12 and 26 weeks. All of the test devices showed marked degradation at all time points, but interestingly, while they initially appeared to degrade quickly, they did not continue to degrade as rapidly. The in vivo study showed that at two weeks, it appeared that TD1 and TD3 showed the most rapid degradation. After four weeks, degradation of TD1, TD2 and TD3 were similar, while TD4 showed less degradation. At 12 weeks, degradation of TD2, TD3 and TD4 were similar, while TD1 appeared considerably more degraded than any of the other test devices. At 26 weeks, no cross-linked bovine tendon collagen was present, there were some remnants of all test devices still present (in the form of tissue discoloration), and the native microbial cellulose was still present as implanted.

Figure 13:
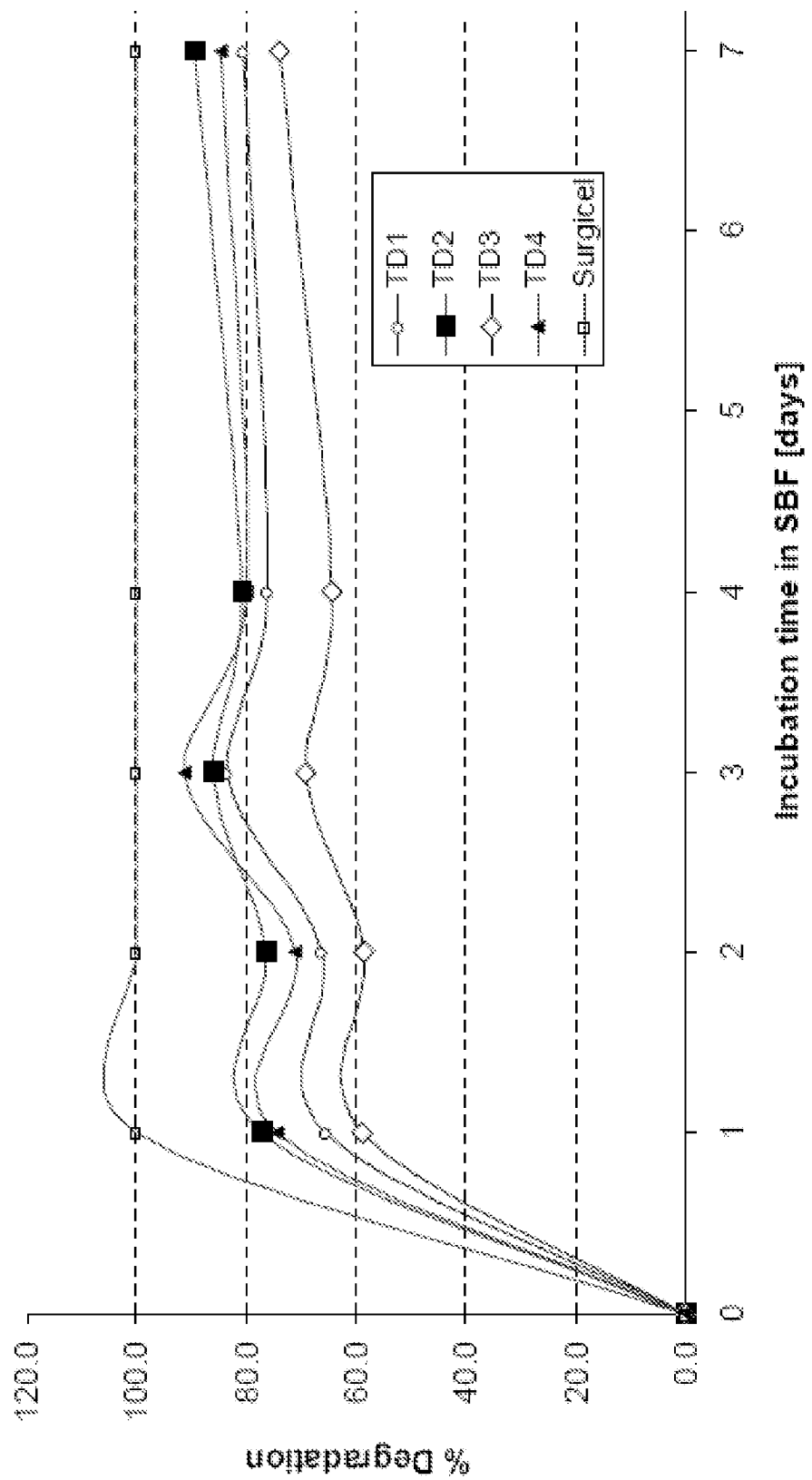
FIG. 13 is a graphical representation of in vitro degradation profiles for irradiated oxidized cellulose samples according to the present disclosure that were used in the in vivo studymeasured against a commercial oxidized cellulose sample of the prior art.

A similar behavior was observed for the samples (TD1-TD4) previously tested in the in vivo study above, during an accelerated in vitro degradation study. The in vitro study of TD1-TD4 against a control sample of Johnson & Johnson Surgicel®, showed a very rapid initial degradation of irradiated oxidized cellulose samples over the first 48 hours of incubation in SBF (pH=7.4) at 55° C. FIG. 13 graphically depicts the degradation results of the in vitro study. The study showed that for TD1-TD4, this rapid degradation levels off at 72-96 hours achieving a plateau.

Collected tissue samples from the in vivo implant sites were fixed in 10% neutral buffered formalin (NBF) and sections through the approximate center of the implant site were taken and embedded in paraffin. Hematoxylin and eosin (H & E) staining and Schiff staining (PAS) were performed. PAS staining was used to evaluate aldehyde (oxidized cellulose) presence. All slides were examined and reviewed by two board certified veterinary pathologists. Evaluation of the tissue response to the test and control devices, including scoring the degree of vascularization, fibrosis, and immune response, of the test and control devices and scoring the degree of irritation of the tissue at the implant site were performed, following the ISO 10993 (2007), part 6, annex E guidelines for evaluation of local biological effects after implantation.

Microscopic evaluation revealed that TD1 and TD4 demonstrated notable loss of material apparent by 12 weeks, and this was comparable in degradation to the cross-linked bovine tendon collagen. TD2 and TD3 had delayed loss of implant, with notable loss not occurring until the 26-week time point. The native microbial cellulose implant showed little to no sign of degradation over the entire period of study.

The inflammatory response to the implant materials was consistent with a foreign body response, characterized by variable numbers of macrophages, foreign body giant cells and with minimal to mild numbers (a score of 1 to 2) of neutrophils. Eosinophils were not uncommon and plasma cells were rarely seen. Fibrosis generally consisted of narrow to moderately thick bands, with the exception of the native microbial cellulose, which presented with increased fibrous capsule formation around the implant at 12 weeks. The total irritancy score was calculated from the sum of the overall inflammatory response (times two), vascularity, and fibrosis pathology scores. The total irritancy score was used to determine the following severity grade for irritant status:

Non-irritant (0.0 to 2.9)

Slight irritant (3.0 to 8.9)

Moderate irritant (9.0 to 15.0)

Severe irritant (>15.0)

Average ranked irritation scores were calculated for each test device at each time point by subtracting the average irritancy score for either CD1 or CD2 from each test device, and were based upon the guidelines as described in ISO 10993, part 6, Annex E (informative) "Examples of evaluation of local biological effects after implantation" for scoring of histology. Tables 12 and 13, below, show the average irritancy scores for the samples against each of control CD1 and CD2 respectively.

The inflammatory reaction to TD4 (including the numbers of macrophages and giant cells) was most prominent at the early time points of all the test materials. These findings are consistent with a very rapidly absorbed material. At 12 and 26 weeks, macrophages and giant cells again predominated for all the test materials, but the highest scores were seen in proximity to TD2, and to a lesser extent, TD3. This finding likely indicates that these materials were resorbing more slowly than was the TD4 material.

The four test materials were compared to the control implants (native microbial cellulose and cross-linked bovine tendon collagen) and were considered to be either non-irritants or slight irritants at 2, 12 or 26 weeks. At the 4-week time point only, TD1 and TD4 were considered to be moderate irritants when compared to the native microbial cellulose.

TABLE 12

| | TD1-TD4 against CD1 | | | |
|---|---|---|---|---|
| | TD1 | TD2 | TD3 | TD4 |
| 2 weeks | 2.75 | 0.25 | 4.50 | 4.75 |
| 4 weeks | 2.75 | 0.50 | 0.00 | 6.50 |
| 12 weeks | 0.75 | 0.00 | 0.50 | 0.00 |
| 26 weeks | 2.75 | 8.50 | 3.50 | 1.50 |

TABLE 13

| | TD1-TD4 against CD2 | | | |
| --- | --- | --- | --- | --- |
| | TD1 | TD2 | TD3 | TD4 |
| 2 weeks | 0.25 | 0.00 | 2.00 | 2.25 |
| 4 weeks | 8.50 | 6.25 | 5.50 | 12.25 |
| 12 weeks | 5.00 | 2.25 | 4.75 | 3.75 |
| 26 weeks | 0.00 | 3.33 | 0.00 | 0.00 |

Although the present disclosure has been described in accordance with several embodiments, it should be understood that various changes, substitutions, and alterations can be made herein without departing from the spirit and scope of the present disclosure, for instance as indicated by the appended claims. Thus, it should be appreciated that the scope of the present disclosure is not intended to be limited to the particular embodiments of the process, manufacture, composition of matter, methods and steps described herein. For instance, the various features as described above in accordance with one embodiment can be incorporated into the other embodiments unless indicated otherwise. Furthermore, as one of ordinary skill in the art will readily appreciate from the present disclosure, processes, manufacture, composition of matter, methods, or steps, presently existing or later to be developed that perform substantially the same function or achieve substantially the same result as the corresponding embodiments described herein may be utilized according to the present disclosure.

It will be appreciated by those skilled in the art that various modifications and alterations of the invention can be made without departing from the broad scope of the appended claims. Some of these have been discussed above and others will be apparent to those skilled in the art.

The invention claimed is:

1. A biomaterial precursor reactive mixture comprising:
    a reactive mixture of:
    (a) an irradiated cellulose; and
    (b) an oxidizing agent;
    wherein the reaction product thereof is a non-pyrogenic resorbable biomaterial.

2. The reactive mixture of claim 1 wherein the irradiated cellulose is microbial-derived cellulose.

3. The reactive mixture of claim 2 wherein the microbial-derived cellulose is derived from *Gluconacetobacter xylinus*.

4. The reactive mixture of claim 1 wherein the reaction product has a degree of oxidation in the range of about 20 percent to about 70 percent.

5. An implant for tissue replacement or augmentation comprising:
    a porous body of irradiated oxidized cellulose, formed by reacting irradiated cellulose with an oxidizing agent, wherein the body forms a heterogeneous three-dimensional fibrillar network.

6. The implant of claim 5 wherein the implant has a first rigid state.

7. The implant of claim 6 wherein the implant has a second hydrated state, and wherein the implant transitions from the first rigid state to the second hydrated state upon hydration by a biocompatible fluid.

8. The implant of claim 7 wherein a surface of the implant in the hydrated state is conformable to an anatomical surface.

9. The implant of claim 8 wherein the anatomical surface is a surface of soft tissue.

10. The implant of claim 9, wherein the soft tissue is dural tissue.

11. The implant of claim 7 wherein a surface of the implant in the hydrated state is conformable to a surface of a secondary medical device.

12. The implant of claim 5, wherein the porous body has an in vitro degradation profile under SBF conditions after one week in the range of about zero percent to 90 percent.

13. The implant of claim 5, wherein the porous body has an in vitro degradation profile under SBF conditions after four weeks in the range of about 20 percent to 80 percent.

14. The implant of claim 5, wherein the implant has a water holding capacity (WHC) of at least 7.0, and wherein the oxidizing agent has a concentration of at least approximately 0.3M.

15. The implant of claim 5, wherein the implant has a surface area and a water holding capacity (WHC), and wherein the WHC to surface area ratio is at least 2.7:1.

16. The implant of claim 5, wherein the implant is a scaffold or carrier for an active agent.

17. The implant of claim 16, wherein the active agent is impregnated within the porous body.

18. The implant of claim 16, wherein the active agent is coated onto a surface of the implant.

19. The implant of claim 16, wherein the active agent is selected from the group consisting of bone marrow, autograft, osteoinductive small molecules, osteogenic material, stem cells, bone morphogenic proteins, antibacterial agents, calcium phosphate ceramics, and mixtures and blends thereof.

20. The implant of claim 7, wherein the implant is substantially translucent in the hydrated state.

21. A method of producing a body of oxidized cellulose comprising the steps of:
    (a) irradiating a body of cellulose so as to form an irradiated body of cellulose, and
    (b) reacting the irradiated body of cellulose with an oxidizing agent so as to form a body of oxidized cellulose;
    wherein the body of oxidized cellulose is non-pyrogenic, porous, and resorbable.

22. The method of claim 21 further comprising the step of at least partially dehydrating the body of irradiated cellulose.

23. The method of claim 21 further comprising the step of at least partially dehydrating the body of oxidized cellulose.

24. The method of claim 22, wherein the step of dehydrating the body of irradiated cellulose is performed by mechanically pressing the cellulose body.

25. The method of claim 23, wherein the step of dehydrating the body of oxidized cellulose is performed by critical point drying using supercritical carbon dioxide.

26. The method of claim 21, wherein the oxidizing agent is selected from the group consisting of metaperiodate, hypochlorite, dichromate, peroxide, permanganate or nitrogen dioxide.

27. The method of claim 26, wherein the oxidizing agent is sodium metaperiodate.

28. The method of claim 27, wherein the cellulose and metaperiodate react in a molar ratio range of 1:1 to about 1:160 of cellulose to metaperiodate.

29. The method of claim 28, wherein the cellulose and metaperiodate react in a molar ratio range of 1:1 to about 1:120 of cellulose to metaperiodate.

30. The method of claim 21, wherein the oxidizing agent has a concentration range of about 0.05M to about 0.5M in the reaction.

31. The method of claim 30, wherein the oxidizing agent has a concentration range of about 0.2M to 0.4M in the reaction.

32. The method of claim 21, wherein the oxidizing agent and the cellulose react for about 0.1 hours to about 24 hours.

33. The method of claim 32, wherein the oxidizing agent and the cellulose react for about 0.1 hours to about 6 hours.

34. The method of claim 21, wherein the body of oxidized cellulose has a degree of oxidation of at least about 25% after one hour of reacting between the oxidizing agent and the irradiated cellulose.

35. The method of claim 21 wherein the body of oxidized cellulose has a degree of oxidation of at least about 40% after two hours of reacting between the oxidizing agent and the irradiated cellulose.

36. The method of claim 21 wherein the body of oxidized cellulose has a degree of oxidation of about 20% to about 70% after reacting between the oxidizing agent and the irradiated cellulose.

37. The method of claim 21 wherein the irradiating step comprises irradiating in the range of about 10 kGy to about 100 kGy.

38. The method of claim 21 wherein the irradiating step comprises irradiating in the range of about 20 kGy to about 40 kGy.

39. The method of claim 21 wherein the irradiating step comprises transmitting γ-radiation.

40. The method of claim 21, further comprising the step of contacting any one of the body of cellulose, the irradiated body of cellulose, or the body of oxidized cellulose, with one or more active agents.

41. The method of claim 21, wherein the step of irradiating includes only a single dose of radiation.

42. The method of claim 21, wherein the step of irradiating includes up to five doses of radiation.

* * * * *